US006812328B2

(12) United States Patent
Ho et al.

(10) Patent No.: US 6,812,328 B2
(45) Date of Patent: Nov. 2, 2004

(54) LOW OXYGEN AFFINITY MUTANT HEMOGLOBINS

(75) Inventors: Chien Ho, Pittsburgh, PA (US); Ching-Hsuan Tsai, Pittsburgh, PA (US); Tsuei-Yun Fang, Yunlin (TW); Tong-Jian Shen, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 121 days.

(21) Appl. No.: 09/986,666

(22) Filed: Nov. 9, 2001

(65) Prior Publication Data

US 2002/0151468 A1 Oct. 17, 2002

Related U.S. Application Data

(62) Division of application No. 09/598,218, filed on Jun. 2, 2000, now Pat. No. 6,486,123.

(51) Int. Cl.[7] .............................................. A61K 35/14
(52) U.S. Cl. ........................................ 530/385; 514/6
(58) Field of Search ............................... 530/385; 514/6

(56) References Cited

U.S. PATENT DOCUMENTS

| 5,028,588 A | 7/1991 | Hoffman et al. |
| 5,753,465 A | 5/1998 | Ho et al. |
| 5,843,888 A | 12/1998 | Ho et al. |

OTHER PUBLICATIONS

Honig et al. , 1990; Am J. Hematology 34(3): 199–203.*
Dickerson, R.E., et al. *Hemoglobin: Structure, Function, Evolution, and Pathology*, pp 22–24, Benjamin/Cummings, Menlo Park, CA (1983).
Mulder, A.G., et al., *J. Cell Comp. Physiol.* 5:383 (1934).
Bunn, H.F., et al. *J. Exp. Med.* 129:909 (1969).
Chada, K., et al., *Nature (London)* 314:377 (1985).
Townes, T. M., et al. *EMBO J.* 4:1715 (1985).
Swanson, M F et al. *Bio Technology* 10:557 (1992).
Groebe, D.R., et al., *Protein Expression and Purification* 3:134 (1992).
Wagenbach, M., et al. *Bio/Technology* 9:57 (1991).
DeLiano, J.J., et al. *Proc. Natl. Acad. Sci. USA* 90:918 (1993).
Hoffman, S.J., et al. *Proc. Natl. Acad. Sci. USA* 87:8521 (1990).
Herman, R.A., et al. *Biochemistry* 31:8619 (1992).
Shen, T.J., et al. *Proc. Natl. Acad. Sci. USA* 90:8108 (1993).
Bunn, H.F., et al. eds. *Hemoglobin: Molecular, Genetic and Clinical Aspects* W.B Saunders. Co., Philadelphia, PA) pp. 37–69 (1986).
Kavanaugh, J.S., et al. *Biochemistry* 31:8640 (1992).
Perutz, M.F., et al. *Mechanisms of Cooperativity and Allosteric Regulation in Proteins* pp 19–23. Cambridge University Press (1990).
Shaanan, B., et al. *J. Mol. Biol. 171*:31 (1983).
Schneider, R. G., et al. *Biochim. Brophys. Acta. 400*:365 (1975).
Bonaventura, J., et al. *J. Biol. Chem 243*:980 (1968).
Perutz, M.F. *Nature 228*: 726 (1970).
Baldwin, J.M., et al. *J. Mol. Biol. 129*: 175 (1979).
Baldwin, J.M., *J. Mol. Biol. 136*: 103 (1980).
Ferm. G., et al. *J. Mol. Biol. 175*: 159 (1984).
Moo–Penn, W.F., et al. *FEBS Lett. 92*:53 (1978).
O'Donnell, J K , et al. *J. Biol. Chem. 269*:27692 (1994).
Baudin. V., et al. *Biochim. Biophys. Acta. 1159*:223 (1992).
Isai. C.–H., et al. *Biochemistry 38*:8751 (1999).
Jeong, S.T., et al., *Biochemistry 38*:13433 (1999).
Kim. H.–W., et al. *Proc. Natl. Acad. Sci. USA 91*:11547 (1994).
Kim. H.–W., et al. *Biochemistry 35*:6620–6627 (1996).
Ho, C., et al., *Blood Substitutes: Present and Future Perspectives of Blood Substitutes (Isuchida, F. Ed.)*. Elsevier Science SA. Lausanne. Switzerland, pp. 281–296 (1998).
Kim. H.–W., et al., *J. Mol. Biol. 248*:867 (1995).
Carver, T.F., et al. *J. Biol. Chem. 267*: 14443 (1992).
Brantley, R.E., Jr., et al. *J. Biol. Chem. 268*: 6995 (1993).
Eich. R.F., et al. *Biochemistry 35*: 6976 (1996).
Doherty, Dild. et al. Nature Bio Tech 16:672 (1998).
Fung, I. W.–M., et al. *Biochemistry 14*:2526 (1975).
Russu. I.M., et al. *Biochem Biophys Acta 914*:40 (1987).
Puius, T.A., et al *Biochemistry 37*: 9258 (1998).
Shen, T.–J., et al. *Protein Eng. 10*: 1085 (1997).
Kunkel, T.M. et al., *Proc. Natl. Acad. Sci. USA 82*:488 (1985).
Hayashi, A., et al. *Biochem. Biophys. Acta 310*:309 (1973).
Antonini, F., *Physiol. Rev. 45*: 123 (1965).
Plateau, P., et al. *J. Am. Chem. Soc. 104*: 7310 (1982).
Wyman, J., *Adv. Protein Chem.* 4:107 (1948).
Wyman, J., *Adv. Protein Chem.* 19:233 (1964).
Dalvit, C., et al., *Biochemistry 24*: 3398 (1985).
Levy et al., *Biochemistry* 29: 9311 (1990).
Levy, et al., *Biophys. J. 61*: 750 (1992).
Blumberg, et al., *Adv. Chem. Series 100*: 271 (1991).
Barrick, D., et al. *Nat. Struct. Biol* 4:78 (1997).
Ho, C., *Adv. Protein Chem.* 43:153 (1992).
Sun, D.P., et al. *Biochemistry 36*:6663 (1997).
Simplaceanu. et al. *Biophys. J., 79*:1146 (2000).
Takahashi, S. et al. *Biochemistry* 19:5196 (1980).
La Mar, G.N., et al. *Biochem. Biophys. Res. Commun.* 96:1172 (1980).
Craescu, C.T., et al., *Eur. J. Biochem 181*: 87 (1989).
R.M. Winslow, et al., Eds. *Blood Substitutes Physiological Basis of Efficacy* (Birkhauser, Boston, Mass.) pp 82–84 (1995).

* cited by examiner

Primary Examiner—Karen Cochrane Carlson
(74) Attorney, Agent, or Firm—ReedSmith LLP

(57) ABSTRACT

Non-naturally occurring mutant hemoglobins rHb (βN108Q) and rHb (βL105W) are provided that have a lower oxygen affinity than that of native hemoglobin, but high cooperativity in oxygen binding. rHb (βN108Q) also exhibits enhanced stability against autoxidation. The mutant hemoglobins are preferably produced by recombinant DNA techniques. Such mutant hemoglobins may be used as a component of a blood substitute and hemoglobin therapeutics.

15 Claims, 20 Drawing Sheets

```
p:tac
    .......
AAATGAGCTG TTGACAATTA ATCATCGGCT CGTATAATGT GTGGAATTGT GAGCGGATAA
                 EcoRI  SacI     KpnISmaI
CAATTTCACA CAGGAAACAG AATTCGAGCT CGGTACCCGG GCTACATGGA GATTAACTCA
                                 RBS          |-> α-globin
ATCTAGAGGG TATTAATAAT GTATCGCTTA AATAAGGAGG AATAACATAT GGTGCTGTCT

CCTGCCGACA AGACCAACGT CAAGGCCGCC TGGGGTAAGG TCGGCGCGCA CGCTGGCGAG

TATGGTGCGG AGGCCCTGGA GAGGATGTTC CTGTCCTTCC CCACCACCAA GACCTACTTC

CCGCACTTCG ATCTGAGCCA CGGCTCTGCC CAGGTTAAGG GCCACGGCAA GAAGGTGGCC

GACGCGCTGA CCAACGCCGT GGCGCACGTG GACGACATGC CCAACGCGCT GTCCGCCCTG

AGCGACCTGC ACGCGCACAA GCTTCGGGTG GACCCGGTCA ACTTCAAGCT CCTAAGCCAC

TGCCTGCTGG TGACCCTGGC CGCCCACCTC CCCGCCGAGT TCACCCCTGC GGTGCACGCC
                                                              ->|
TCCCTGGACA AGTTCCTGGC TTCTGTGAGC ACCGTGCTGA CCTCCAAATA CCGTTAAACT
                                 RBS          |-> β-globin
AGAGGGTATT AATAATGTAT CGCTTAAATA AGGAGGAATA ACATATGGTG CACCTGACTC

CTGAGGAGAA GTCTGCCGTT ACTGCCCTGT GGGGCAAGGT GAACGTGGAT GAAGTTGGTG

GTGAGGCCCT GGGCAGGCTG CTGGTGGTCT ACCCTTGGAC CCAGAGGTTC TTTGAGTCCT

TTGGGGATCT GTCCACTCCT GATGCTGTTA TGGGCAACCC TAAGGTGAAG GCTCATGGCA

AGAAAGTGCT CGGTGCCTTT AGTGATGGCC TGGCTCACCT GGACAACCTC AAGGGCACCT

TTGCCACACT GAGTGAGCTG CACTGTGACA AGCTGCACGT GGATCCTGAG AACTTCAGGC
           β108Asn->Gln
TCCTGGGACA AGTACTGGTC TGTGTGCTGG CCCATCACTT TGGCAAAGAA TTCACCCCAC

CAGTGCAGGC TGCCTATCAG AAAGTGGTGG CTGGTGTGGC TAATGCCCTG GCCCACAAGT
      ->|SphI     rrB(5S,T1,T2)
ATCACTAAGC ATGCATCTGT TTTGGCGGAT GAGAGAAGAT TTTCAGCCTG ATACAGATTA
           NsiI
.......
```

FIG. 1A

```
                                                          . . . . . .
p:tac
AAATGAGCTG TTGACAATTA ATCATCGGCT CGTATAATGT GTGGAATTGT GAGCGGATAA
                    EcoRI   SacI      KpnISmaI
CAATTTCACA CAGGAAACAG AATTCGAGCT CGGTACCCGG GCTACATGGA GATTAACTCA
                                    RBS        |-> α-globin
ATCTAGAGGG TATTAATAAT GTATCGCTTA AATAAGGAGG AATAACATAT GGTGCTGTCT

CCTGCCGACA AGACCAACGT CAAGGCCGCC TGGGGTAAGG TCGGCGCGCA CGCTGGCGAG

TATGGTGCGG AGGCCCTGGA GAGGATGTTC CTGTCCTTCC CCACCACCAA GACCTACTTC

CCGCACTTCG ATCTGAGCCA CGGCTCTGCC CAGGTTAAGG GCCACGGCAA GAAGGTGGCC

GACGCGCTGA CCAACGCCGT GGCGCACGTG GACGACATGC CCAACGCGCT GTCCGCCCTG

AGCGACCTGC ACGCGCACAA GCTTCGGGTG GACCCGGTCA ACTTCAAGCT CCTAAGCCAC

TGCCTGCTGG TGACCCTGGC CGCCCACCTC CCCGCCGAGT TCACCCCTGC GGTGCACGCC
                                                              ->|
TCCCTGGACA AGTTCCTGGC TTCTGTGAGC ACCGTGCTGA CCTCCAAATA CCGTTAAACT
                                    RBS        |-> β-globin
AGAGGGTATT AATAATGTAT CGCTTAAATA AGGAGGAATA ACATATGGTG CACCTGACTC

CTGAGGAGAA GTCTGCCGTT ACTGCCCTGT GGGGCAAGGT GAACGTGGAT GAAGTTGGTG

GTGAGGCCCT GGGCAGGCTG CTGGTGGTCT ACCCTTGGAC CCAGAGGTTC TTTGAGTCCT

TTGGGGATCT GTCCACTCCT GATGCTGTTA TGGGCAACCC TAAGGTGAAG GCTCATGGCA

AGAAAGTGCT CGGTGCCTTT AGTGATGGCC TGGCTCACCT GGACAACCTC AAGGGCACCT

TTGCCACACT GAGTGAGCTG CACTGTGACA AGCTGCACGT GGATCCTGAG AACTTCAGGT
β105Leu->Trp
GGCTAGGCAA CGTGCTGGTC TGTGTGCTGG CCCATCACTT TGGCAAAGAA TTCACCCCAC

CAGTGCAGGC TGCCTATCAG AAAGTGGTGG CTGGTGTGGC TAATGCCCTG GCCCACAAGT
     ->|SphI        rrB(5S,T1,T2)
ATCACTAAGC ATGCATCTGT TTGGCGGAT GAGAGAAGAT TTTCAGCCTG ATACAGATTA
            NsiI
. . . . . .
```

FIG. 1B

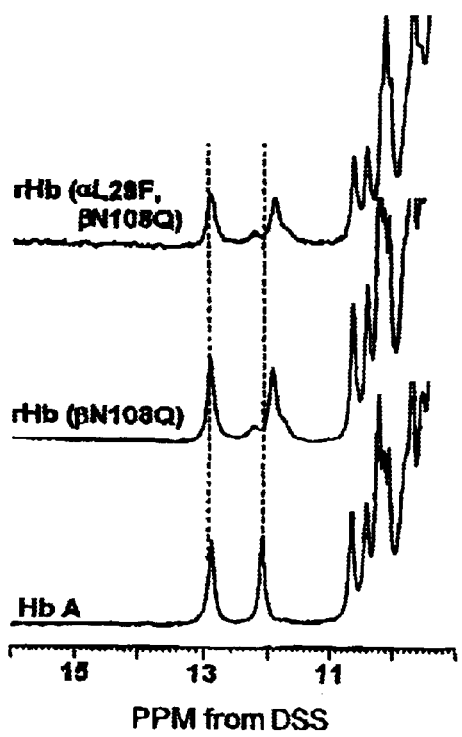
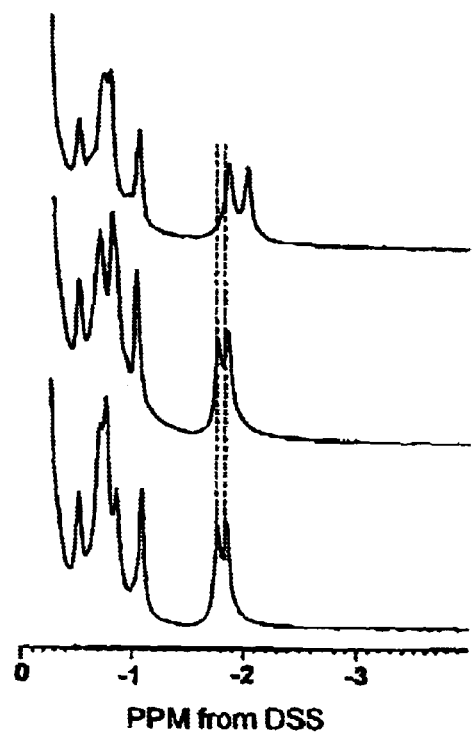
FIG. 6A  FIG. 6B

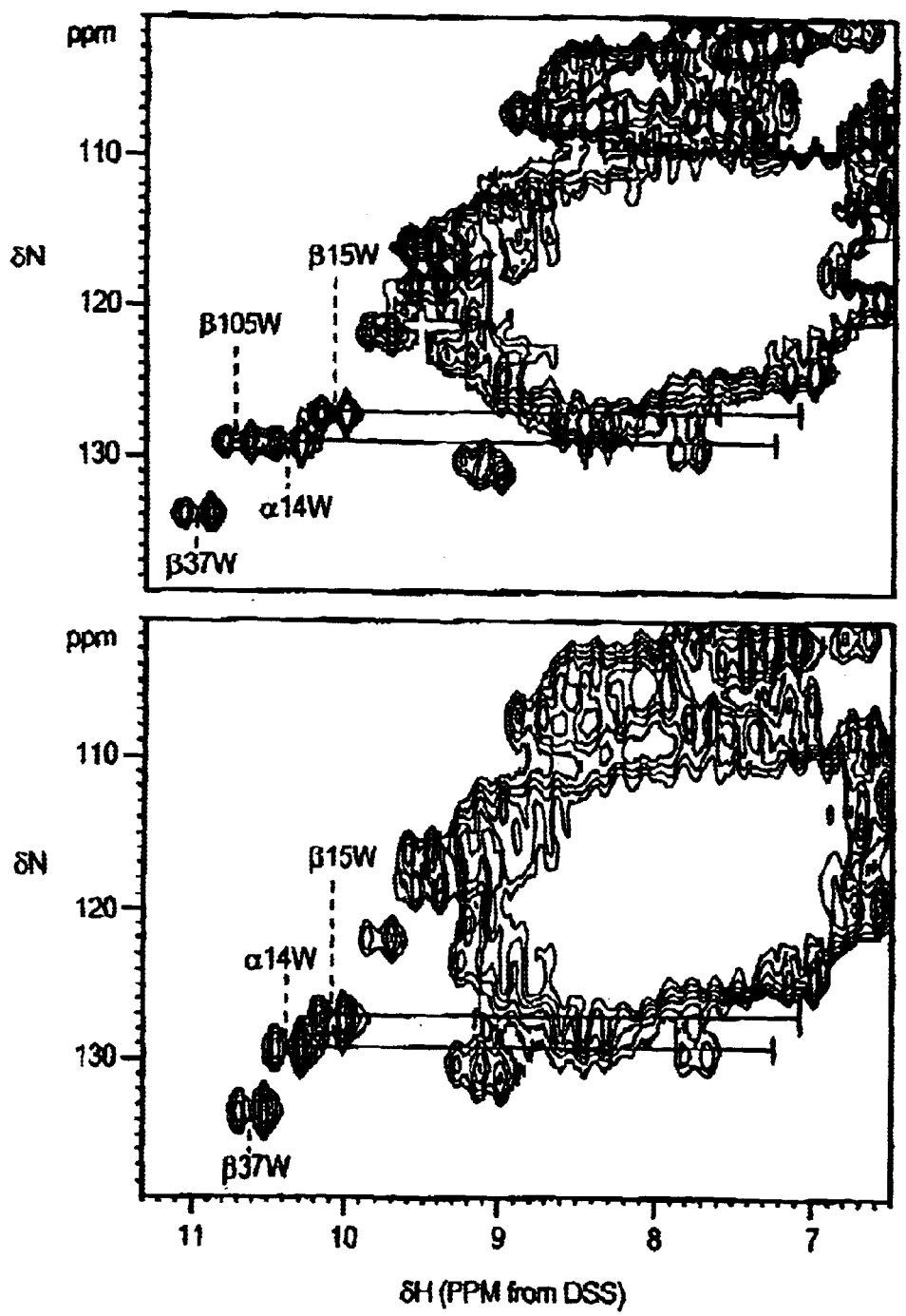

FIG. 12A
FIG. 12B
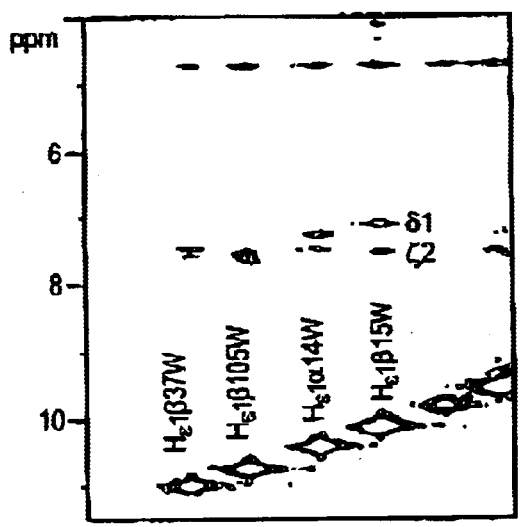
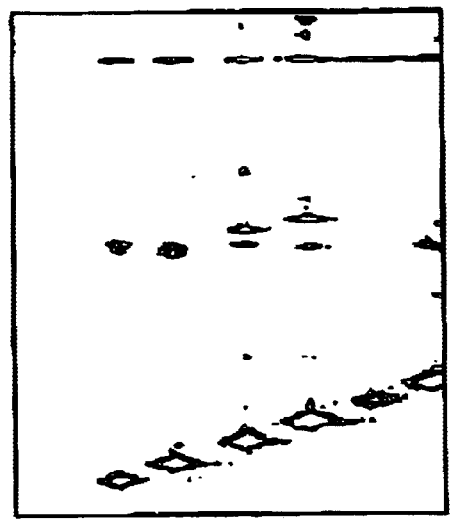
FIG. 12C
FIG. 12D

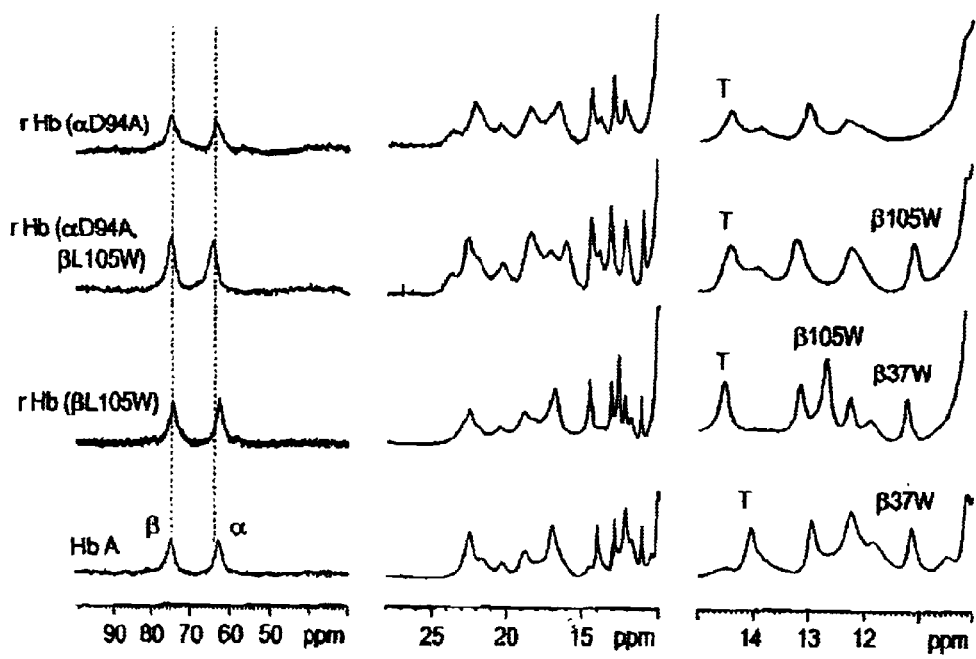
FIG. 13A  FIG. 13B  FIG. 13C

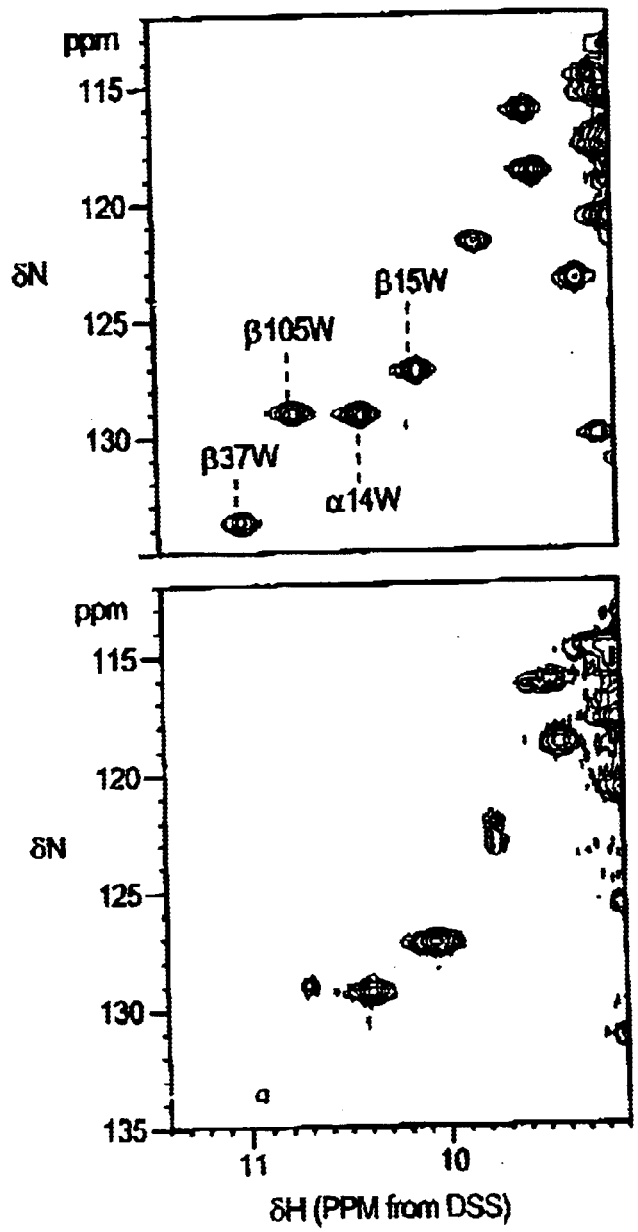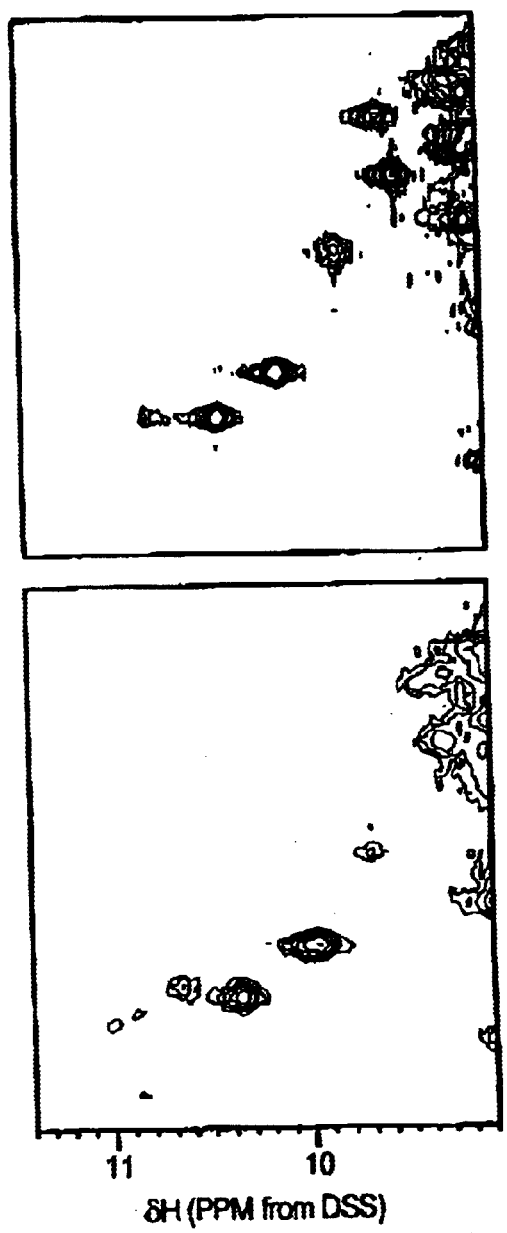
FIG. 17A  FIG. 17B  FIG. 17C  FIG. 17D

SEQUENCE LISTING

<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: DESCRIPTION OF ARTIFICIAL SEQUENCE: Primer to introduce betaN108 Q mutation into plasmid pHE2

```
<400> SEQUENCE: 1
cgtctgctgg gtcaggtact agtttgcg                                           28

<210> SEQ ID NO 2
<211> LENGTH: 30
<212> TYPE: DNA
<213> ORGANISM: Artificial Sequence
<220> FEATURE:
<223> OTHER INFORMATION: DESCRIPTION OF ARTIFICIAL SEQUENCE:  Primer to
      introduce mutation alphaD94A into plasmid pHE2

<400> SEQUENCE: 2
ctgcgtgttg ctccggtcaa cttcaaactg                                         30

<210> SEQ ID NO 3
<211> LENGTH: 29
<212> TYPE: DNA
<213> ORGANISM: Artificial Sequence
<220> FEATURE:
<223> OTHER INFORMATION: DESCRIPTION OF ARTIFICIAL SEQUENCE:  Primer to
      introduce betaL105 W mutation into plasmid pHE2

<400> SEQUENCE: 3
ggaaaacttc cgatggctgg gtaacgtac                                          29

<210> SEQ ID NO 4
<211> LENGTH: 27
<212> TYPE: DNA
<213> ORGANISM: Artificial Sequence
<220> FEATURE:
<223> OTHER INFORMATION: DESCRIPTION OF ARTIFICIAL SEQUENCE:  Primer to
      introduce betaN108 Q mutation into plasmid pHE7

<400> SEQUENCE: 4
acagaccagt acttgtccca ggagcct                                            27

<210> SEQ ID NO 5
<211> LENGTH: 1140
<212> TYPE: DNA
<213> ORGANISM: Homo sapiens

<400> SEQUENCE: 5
aaatgagctg ttgacaatta atcatcggct cgtataatgt gtggaattgt gagcggataa        60
caatttcaca caggaaacag aattcgagct cggtacccgg gctacatgga gattaactca       120
atctagaggg tattaataat gtatcgctta ataaggagg ataacatat ggtgctgtct         180 cctgccgaca agaccaacgt caaggccgcc tggggtaagg tcggcgcgca cgctggcgag       240
tatggtgcgg aggccctgga gaggatgttc ctgtccttcc ccaccaccaa gacctacttc      300
ccgcacttcg atctgagcca cggctctgcc caggttaagg ccacggcaa gaaggtggcc       360 gacgcgctga ccaacgccgt ggcgcacgtg acgacatgc ccaacgcgct gtccgccctg       420
agcgacctgc acgcgcacaa gcttcgggtg gacccggtca acttcaagct cctaagccac     480
tgcctgctgg tgaccctggc cgcccacctc cccgccgagt tcaccctgc ggtgcacgcc      540 tccctggaca gttcctggc ttctgtgagc accgtgctga cctccaaata ccgttaaact      600
agagggtatt aataatgtat cgcttaaata aggaggaata acatatggtg cacctgactc     660
ctgaggagaa gtctgccgtt actgccctgt ggggcaaggt gaacgtggat gaagttggtg     720
gtgaggccct gggcaggctg ctggtggtct acccttggac ccagaggttc tttgagtcct     780
ttggggatct gtccactcct gatgctgtta tgggcaaccc taaggtgaag gctcatggca    840
```

```
agaaagtgct cggtgccttt agtgatggcc tggctcacct ggacaacctc aagggcacct      900
ttgccacact gagtgagctg cactgtgaca agctgcacgt ggatcctgag aacttcaggc      960
tcctgggaca agtactggtc tgtgtgctgg cccatcactt tggcaaagaa ttcaccccac     1020
cagtgcaggc tgcctatcag aaagtggtgg ctggtgtggc taatgccctg gcccacaagt     1080
atcactaagc atgcatctgt tttggcggat gagagaagat tttcagcctg atacagatta     1140

<210> SEQ ID NO 6
<211> LENGTH: 36
<212> TYPE: DNA
<213> ORGANISM: Artificial Sequence
<220> FEATURE:
<223> OTHER INFORMATION: DESCRIPTION OF ARTIFICIAL SEQUENCE: Primer to
      introduce betaL105 W mutation into plasmid pHE7

<400> SEQUENCE: 6
cctgagaact tcaggtggct aggcaacgtg ctggtc                                36

<210> SEQ ID NO 7
<211> LENGTH: 1140
<212> TYPE: DNA
<213> ORGANISM: Homo sapiens

<400> SEQUENCE: 7
aaatgagctg ttgacaatta atcatcggct cgtataatgt gtggaattgt gagcggataa       60
caatttcaca caggaaacag aattcgagct cggtacccgg gctacatgga gattaactca      120
atctagaggg tattaataat gtatcgctta ataaggagg aataacatat ggtgctgtct      180
cctgccgaca agaccaacgt caaggccgcc tggggtaagg tcggcgcgca cgctggcgag      240
tatggtgcgg aggccctgga gaggatgttc ctgtccttcc ccaccaccaa gacctacttc      300
ccgcacttcg atctgagcca cggctctgcc caggttaagg gccacggcaa gaaggtggcc      360
gacgcgctga ccaacgccgt ggcgcacgtg gacgacatgc ccaacgcgct gtccgccctg      420
agcgacctgc acgcgcacaa gcttcgggtg gacccggtca acttcaagct cctaagccac      480
tgcctgctgg tgaccctggc cgcccacctc cccgccgagt tcacccctgc ggtgcacgcc      540
tccctggaca gttcctggc ttctgtgagc accgtgctga cctccaaata ccgttaaact      600
agagggtatt aataatgtat cgcttaaata aggaggaata acatatggtg cacctgactc      660
ctgaggagaa gtctgccgtt actgccctgt ggggcaaggt gaacgtggat gaagttggtg      720
gtgaggccct gggcaggctg ctggtggtct acccttggac ccagaggttc tttgagtcct      780
ttggggatct gtccactcct gatgctgtta tgggcaaccc taaggtgaag gctcatggca      840
agaaagtgct cggtgccttt agtgatggcc tggctcacct ggacaacctc aagggcacct      900
ttgccacact gagtgagctg cactgtgaca agctgcacgt ggatcctgag aacttcaggt      960
ggctaggcaa cgtgctggtc tgtgtgctgg cccatcactt tggcaaagaa ttcaccccac     1020
cagtgcaggc tgcctatcag aaagtggtgg ctggtgtggc taatgccctg gcccacaagt     1080
atcactaagc atgcatctgt tttggcggat gagagaagat tttcagcctg atacagatta     1140

<210> SEQ ID NO 8
<211> LENGTH: 146
<212> TYPE: PRT
<213> ORGANISM: Homo sapiens

<400> SEQUENCE: 8

Val His Leu Thr Pro Glu Glu Lys Ser Ala Trp Thr Ala Leu Trp Gly
```

```
                        -continued
1               5                    10                      15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                      70                  75                  80

Leu Lys Gly Thr Phe Ala Thr Leu Ser Glu Leu His Cys Asp Lys Leu
                    85                  90                  95

His Val Asp Pro Glu Asn Phe Arg Leu Leu Gly Asn Val Leu Val Cys
                100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
        130                 135                 140

Tyr His
145
```

LOW OXYGEN AFFINITY MUTANT HEMOGLOBINS

This application is a divisional application of Ser. No. 09/598,216, filed Jun. 21, 2000, now U.S. Pat. No. 6,486,123.

The present invention was developed in part with government support under grant numbers HL-24525 and HL-58249. The government has certain rights in this invention.

FIELD OF THE INVENTION

This invention relates generally to novel mutant hemoglobins and more particularly relates to recombinant mutant hemoglobins "rHb (βN108Q)" (alternative designation "rHb (β108Asn→Gln)") and "rHb (βL105W)" (alternative designation "rHb (βL105Leu→Trp") that possess low oxygen affinity, and high cooperativity in oxygen binding. In particular, rHb (βN108Q) exhibits increased resistance to autoxidation as compared to other known low oxygen affinity mutants. This invention further relates to the preparation of mutant hemoglobins using recombinant DNA technology that are useful as substitutes for red blood cells and for hemoglobin-based therapeutics.

BACKGROUND OF THE INVENTION

The prevalence of infectious agents such as HIV and hepatitis in red blood cells of human blood products coupled with blood shortages from lack of suitable donors has led to great interest in the development of red blood cell substitutes, particularly human hemoglobin ("Hb") and its derivatives. Hemoglobin-based oxygen carriers are potential sources of blood substitutes during emergency medical situations. See for example, Winslow, R. M., et al. *Hemoglobin-Based Red Cell Substitutes*, Johns Hopkins University Press, Baltimore (1992) (hereinafter "Winslow, et al. (1992)"), the disclosure of which is incorporated herein by reference.

Hemoglobin is the oxygen-carrying component of blood, circulated through the blood stream inside erythrocytes (red blood cells). Human normal adult hemoglobin ("Hb A") is a tetrameric protein with a molecular weight of about 64,500 containing two identical a chains having 141 amino acid residues each and two identical β chains having 146 amino acid residues each, with each also bearing prosthetic groups known as hemes. The erythrocytes help maintain hemoglobin in its reduced, functional form. The heme-iron atom is susceptible to oxidation, but may be reduced again by one of two systems within the erythrocyte, the cytochrome $b_5$, and glutathione reduction systems. For a review on hemoglobin, see, Dickerson, R. E., et al. *Hemoglobin: Structure, Function, Evolution, and Pathology*, p. 22–24, Benjamin/Cummings, Menlo Park, Calif. (1983) (hereinafter "Dickerson, et al. (1983)"), the disclosure of which is incorporated herein by reference.

The oxygenation process of Hb A is cooperative, i.e., the binding of the first oxygen molecule enhances the binding of the second, third, and fourth oxygen molecules. The oxygenation process is also regulated by interactions between individual amino acid residues and various solutes, known as heterotropic allosteric effectors. These effectors include ions or molecules such as hydrogen ion, chloride, carbon dioxide, inorganic phosphate, and organic polyanions, such as 2,3-bisphosphoglycerate ("2,3-BPG") and inositol hexaphosphate ("IHP").

Hemoglobin is able to alter its oxygen affinity, thereby increasing the efficiency of oxygen transport in the body, due to its dependence on the allosteric effector 2,3-BPG. 2,3-BPG is present within erythrocytes at a concentration that allows hemoglobin to release bound oxygen to tissues. In the absence of 2,3-BPG, hemoglobin binds oxygen very tightly and does not readily release its bound oxygen. The Hub A molecule alone, were it to be introduced into a subject, would not be able to properly allow oxygen to be delivered to tissues in the body due to a lack of 2,3-BPG, which lowers the oxygen affinity of Hb, in the blood plasma. See, Winslow, et al. (1992). Any Hbs designed to be functional as Hb-based oxygen carriers or hemoglobin therapeutics should be able to deliver oxygen efficiently, i.e., they should load and unload cooperatively as Hb A does inside red blood cells.

The use of cell-free solutions of hemoglobin as a potential oxygen-carrying red cell substitute has been investigated for a long time. See, for example Mulder, A. G., et al., *J. Cell Comp. Physiol.* 5:383 (1934), the disclosure of which is incorporated herein by reference. However, the use of unmodified cell-free human hemoglobin purified from red blood cells suffers from several limitations in addition to contamination and supply limitations noted above, namely, an increase in oxygen affinity due to loss of allosteric effectors, such as 2,3-BPG, and dissociation of Hb tetramers into αβ dimers which are cleared by renal filtration and which can cause long-term kidney damage. See, for example Bunn, H. F., et al. *J. Exp. Med.* 129:909 (1969), the disclosure of which is incorporated herein by reference.

Human globins and hemoglobins have been expressed in the following: transgenic mice, see, for example, Chada, K., et al., *Nature (London)* 314:377 (1985) and Townes, T. M., et al. *EMBO J.* 4:1715 (1985), transgenic swine as described by Swanson, M. E., et al. *Bio/Technology* 10:557 (1992), insect cell cultures as reported by Groebe, D. R., et al., *Protein Expression and Purification* 3:134 (1992), yeast as described by Wagenbach, M., et al. *Bio/Technology* 9:57 (1991) and DeLiano, J. J., et al. *Proc. Natl. Acad. Sci. USA* 90:918 (1993), and *Escherichia coli* ("*E. coli*") as described by Hoffman, S. J., et al. *Proc. Natl. Acad. Sci. USA* 87:8521 (1990), Hernan, R. A., et al. *Biochemistry* 31:8619 (1992), and Shen, T. -J., et al. *Proc. Natl. Acad. Sci. USA* 90:8108 (1993) (hereinafter "Shen, et al. (1993)"), all the disclosures of which are incorporated herein by reference. In many respects, the *E. coli* system is the best choice for such purposes because of its high expression efficiency and the ease of performing site-directed mutagenesis.

The natural N-terminal valine residues of Hb A are known to play important roles in regulating oxygen affinity, the Bohr effect, and interactions with allosteric effectors and anions as reported by Bunn, H. F., et al. eds. *Hemoglobin: Molecular, Genetic and Clinical Aspects* (W. B. Saunders, Co., Philadelphia, Pa.) pp. 37–60 (1986) (hereinafter "Bunn, et al. (1986)"), the disclosure of which is incorporated herein by reference. The extra methionine can alter the N-terminal conformation of the Hb molecule as reported by Kavanaugh, J. S., et al. *Biochemistry* 31:8640 (1992), the disclosure of which is incorporated herein by reference. Hence, the oxygenation properties of Hb depend on the integrity of the N-terminal residue thereby mandating the removal of the extra methionine residues from the N-termini of both the α- and β-globins of the expressed Hb before the *E. coli* system can be used effectively for the production of desired unmodified and mutant Hbs.

The cooperative oxygenation of Hb, as measured by the Hill coefficient ("$n_{max}$") is a convenient measure of its oxygenation properties. See, Dickerson, et al. (1983). Hb A has an $n_{max}$ value of approximately 3 in its binding with $O_2$ under usual experimental conditions. Human abnormal Hbs with amino acid substitutions in the $\alpha_1\beta_2$ (or $\alpha_2\beta_1$) subunit interface generally result in high oxygen affinity and reduced cooperativity in $O_2$ binding compared to Hb A. See, for example, Dickerson, et al. (1983); Bunn, at al (1986) and Perutz, M. F. at al. *Mechanisms of Cooperativity and Allosteric Regulation in Proteins* pp. 19–29, Cambridge University Press (1990), the disclosure of which is incorporated herein by reference.

Hb A in its oxy form (Hb A with oxygen molecules) has a characteristic hydrogen bond between $\alpha$94Asp and $\beta$102Asn in the $\alpha_1\beta_2$ subunit interface as reported by Shaanan, B., et al. *J. Mol. Biol.* 171:31 (1983), the disclosure of which is incorporated herein by reference (hereinafter "Shaanan, et al. (1983)"). Human Hbs with an amino acid substitution at either the $\alpha$94Asp position such as Hb Titusville ($\alpha$94Asp→Asn) (Schneider, R. G., et al. *Biochim. Biophys. Acta.* 400:365 (1975), the disclosure of which is incorporated herein by reference) or the $\beta$102Asn position such as Hb Kansas ($\beta$102Asn→Thr) (Bonaventura, J., et al. *J. Biol. Chem.* 243:980 (1968), the disclosure of which is incorporated herein by reference), as well as others with mutations in the $\alpha_1\beta_2$ subunit interface, exhibit very low oxygen affinity. However, all these Hb mutants which directly disrupt the hydrogen bond between $\alpha$94Asp and $\beta$102Asn in the oxy form of Hb show greatly reduced cooperativity in the binding of oxygen and additionally dissociate easily into dimers when in the ligated state.

It has also been shown that during the transition from the deoxy-to the oxy-state, the $\alpha_1\beta_2$ subunit of Hb A undergoes a sliding movement, while the $\alpha_1\beta_1$ subunit interface remains nearly unchanged (See, Perutz, M. F. *Nature* 228: 726 (1970) ("Perutz (1970)"); Baldwin, J. M., et al. *J. Mol. Biol.* 129: 175 (1979); Baldwin, J. M., *J. Mol. Biol.* 136: 103 (1980); Shaanan, et al. (1983); and Fermi, G., et al. *J. Mol. Biol.* 175: 159 (1984), ("Fermi, et al., (1984)"), the disclosures of which are incorporated herein by reference. There are specific hydrogen bonds, salt bridges, and non-covalent interactions that characterize both subunit interfaces. The Hb molecule also has a lower oxygen affinity in the deoxy quaternary structure (T-structure) than in the oxy quaternary structure (R-structure) See, Dickerson, et al. (1983).

Low oxygen affinity human mutant Hbs which do not involve either $\alpha$94Asp or $\beta$102Asn also exist. For example, Hb Presbyterian ($\beta$108Asn→Lys) (Moo-Penn, W. F., et al. *FEBS Lett.* 92:53 (1978) and O'Donnell, J. K., et al. *J. Biol. Chem.* 269:27692 (1994) (hereinafter "O'Donnell, et al. (1994)"); Hb Yoshizuka ($\beta$108Asn→Asp), O'Donnell, et al. (1994) and recombinant Hb Mequon ($\beta$41Phe→Tyr) (Baudin, V., et al. *Biochim. Biophys. Acta.* 1159:223 (1992), the disclosures of which are incorporated herein by reference, all exhibit low oxygen affinity compared to Hb A, but they all exhibit a variable amount of cooperativity as measured by the Hill coefficient, with n varying from 1.8 to 2.9. Tsai, C. -H., et al. *Biochemistry* 38:8751 (1999) (hereinafter, "Tsai, et al. (1999)") report Hb ($\alpha$96Val→Trp, $\beta$108Asn→Lys) which has low oxygen affinity and a greater tendency to switch to the T quaternary structure. Jeong, S. T., et al., *Biochemistry* 38:13433 (1999) (hereinafter, "Jeong, et al. (1999)") report that Hb ($\alpha$29Leu→Phe, $\alpha$96Val→Trp, $\beta$108Asn→Lys) exhibits low oxygen affinity and high cooperativity combined with resistance to autoxidation.

Shen, et al. (1993) and U.S. Pat. No. 5,753,465, the disclosures of which are incorporated herein by reference, describe an *E. coli* expression plasmid (pHE2) in which synthetic human $\alpha$- and $\beta$-globin genes are coexpressed with the *E. coli* methionine aminopeptidase gene under the control of separate tac promotors. *E. coli* cells transformed with this plasmid express recombinant Hb A (hereinafter "rHb A") from which the N-terminal methionines have been effectively cleaved by the coexpressed methionine aminopeptidase. The resulting rHb A which lacks an N-terminal methionine is identical to the native Hb A in a number of structural and functional properties.

Kim, H. -W., et al. *Proc. Natl. Acad. Sci. USA* 91:11547 (1994) (hereinafter "Kim, et al. (1994)"), and U.S. Pat. No. 5,843,888, the disclosures of which are incorporated herein by reference, describe a non-naturally occurring mutant hemoglobin (rHb($\alpha$96Val→Trp) (alternative designation "rHb ($\alpha$96W)") that has a lower oxygen affinity than that of native hemoglobin, but high cooperativity in oxygen binding.

There remains a need, however, for additional mutant hemoglobin species that can be used as a component of a hemoglobin-based blood substitute or therapeutic agent. Of particular interest is a mutant hemoglobin that possesses low oxygen affinity, high cooperativity in oxygen binding, and increased stability against autoxidation. There is a further need for such a hemoglobin produced by recombinant methods and an efficient expression system for producing such a mutant hemoglobin in high yield, especially for use in a blood substitute product or hemoglobin therapeutics.

SUMMARY OF THE INVENTION

Accordingly, it is a primary object of the present invention to provide mutant human hemoglobins with low oxygen affinity and high cooperativity in oxygen binding.

Another object of the present invention is to provide mutant hemoglobins with low oxygen affinity, high cooperativity in oxygen binding, and increased stability against autoxidation.

Another object of the present invention is to provide non-naturally occurring mutant human hemoglobins with low oxygen affinity and high cooperativity in oxygen binding.

Another object of the present invention is to provide non-naturally occurring mutant human hemoglobins with low oxygen affinity, high cooperativity in oxygen binding, and increased stability against autoxidation.

Another object of the present invention is to provide non-naturally occurring mutant human hemoglobins with low oxygen affinity, high cooperativity in oxygen binding, and preferably with stability against autoxidation that are produced artificially, preferably by recombinant means, and that have the correct heme conformation.

Another object of the present invention is to provide mutant hemoglobins that in a cell-free environment have similar oxygen binding properties as those of human normal adult hemoglobin in red blood cells.

Yet another object of the present invention is to provide mutant hemoglobins with low oxygen affinity and high cooperativity in oxygen binding in which the T-structure is stabilized while the R-structure is undisturbed.

Still another object of the present invention is to provide artificial hemoglobins for use as a hemoglobin-based oxygen carrier/red blood substitute or therapeutic agent.

These and other objects of the present invention are achieved by one or more of the following embodiments.

In one aspect, the invention features a non-naturally occurring mutant human hemoglobin wherein the asparagine residue at position 108 of the $\beta$-chains is replaced by a glutamine residue.

In a preferred embodiment, the hemoglobin possesses low oxygen affinity as compared to human normal adult hemoglobin, high cooperativity in oxygen binding, increased stability against autoxidation, and is produced recombinantly.

In another aspect, the invention features an artificial mutant hemoglobin which in a cell-free enviornment has oxygen binding properties comparable to those of human normal adult hemoglobin in red blood cells wherein said hemoglobin contains a mutation such that the asparagine residue at position 108 of the β-chains is glutamine.

A non-naturally occurring low oxygen affinity mutant hemoglobin with increased stability against autoxidation that has oxygen binding properties comparable to those of human normal adult hemoglobin in the presence of the allosteric effector 2,3-bisphosphoglycerate, wherein the asparagine residue at position 108 of each of the β-chains is replaced by a glutamine residue.

In yet another aspect, the invention features a non-naturally occurring mutant human hemoglobin wherein the leucine residue at position 105 of the β-chains is replaced by a tryptophan residue.

In a preferred embodiment, the hemoglobin possesses low oxygen affinity as compared to human normal adult hemoglobin, high cooperativity in oxygen binding, and is produced recombinantly.

In another aspect, the invention features an artificial mutant hemoglobin which in a cell-free environment has oxygen binding properties comparable to those of human normal adult hemoglobin in red blood cells wherein said hemoglobin contains a mutation such that the leucine residue at position 105 of the β-chains is tryptophan.

A non-naturally occurring low oxygen affinity mutant hemoglobin that has oxygen binding properties comparable to human normal adult hemoglobin in the presence of the allosteric effector 2,3-bisphosphoglycerate, wherein the leucine residue at position 105 of each of the β-chains is replaced by a tryptophan residue.

Other features and advantages of the invention will be apparent from the following description of the preferred embodiment, and from the claims.

DESCRIPTION OF THE DRAWINGS

FIG. 1A is a cDNA sequence (SEQ ID NO: 5) for the alpha- and beta-globin genes for rHb (βN108Q) derived from plasmid pHE7009.

FIG. 1B is a cDNA sequence (SEQ ID NO: 7) for alpha- and beta-globin genes for rHb (β105W) derived from plasmid pHE7004.

FIGS. 6A and 6B are 500-MHz $^1$H-NMR spectra showing exchangeable proton resonances (FIG. 6A) and ring-current shifted proton resonances (FIG. 6B), respectively, of Hb A; rHb (βN108Q), and rHb (αL29W, βL108Q), all in the CO form in 0.1 M sodium phosphate buffer at pH 7.0 and 29° C.

FIGS. 11A and 11B are 600-MHz 2D heteronuclear multiple-quantum coherence ("HMQC") spectra of 5–8% solutions of $^{15}$N-labeled rHb (βL105W) (FIG. 11A) and Hb A (FIG. 11B) in the CO form in 90% $H_2O$/10% $D_2O$ in 0.1 M sodium phosphate at pH 7.0 and 29° C.

FIGS. 12A–12D are 600-MHz 2D NOESY-HMQC ("NOESY"-nuclear Overhauser enhancement spectroscopy) spectra of a 5% solution of $^{15}$N-labeled rHb (βL105W) in the CO form in 90$H_2O$/10% $D_2O$ in 0.1 M sodium phosphate at pH 7.0 and 29° C. recorded at various mixing times: 15 ms (FIG. 12A); 30 ms (FIG. 12B); 60 ms (FIG. 12C); and 100 ms (FIG. 12D).

FIGS. 13A–13C are 300-MHz $^1$H-NMR spectra of 3–6% solutions of Hb A; rHb (βL105W); rHb (αD94A, βL105W); and rHb (rHb (αD94A) in the deoxy form in 0.1 M sodium phosphate at pH 7.0 and 29° C. FIG. 13A shows hyperfine-shifted $N_δH$ resonances of proximal histidines acquired at 300-MHz; FIG. 13B shows hyperfine shifted and exchangeable proton resonances acquired at 300-MHz; and FIG. 13C shows exchangeable proton resonances acquired at 300-MHz. Since rHb (αD94A, βL105W) and rHb (αD94A) easily form met-Hb during the oxygenization process, a small amount of sodium dithionite was added to these NMR samples to diminish the formation of met-Hb.

FIG. 17A–17D are 600-MHz 2D heteronuclear single-quantum coherence ("HSQC") spectra of 5–8% solutions of $^{15}$N-labeled rHb (βL105W) in the CO form in 90% $H_2O$/10% $D_2O$ in 0.1 M sodium phosphate at pH 7.0 and various temperatures in the absence and presence of 2 mM IHP. FIG. 17A—29° C. in the absence of IHP; FIG. 17B—at 29° C. in the presence of 2 mM IHP; FIG. 17C—at 20° C. in the presence of 2 mM IHP; and FIG. 19D—11° C. in the presence of 2 mM IHP.

DETAILED DESCRIPTION OF THE INVENTION

I. Definitions

Figure 2A:
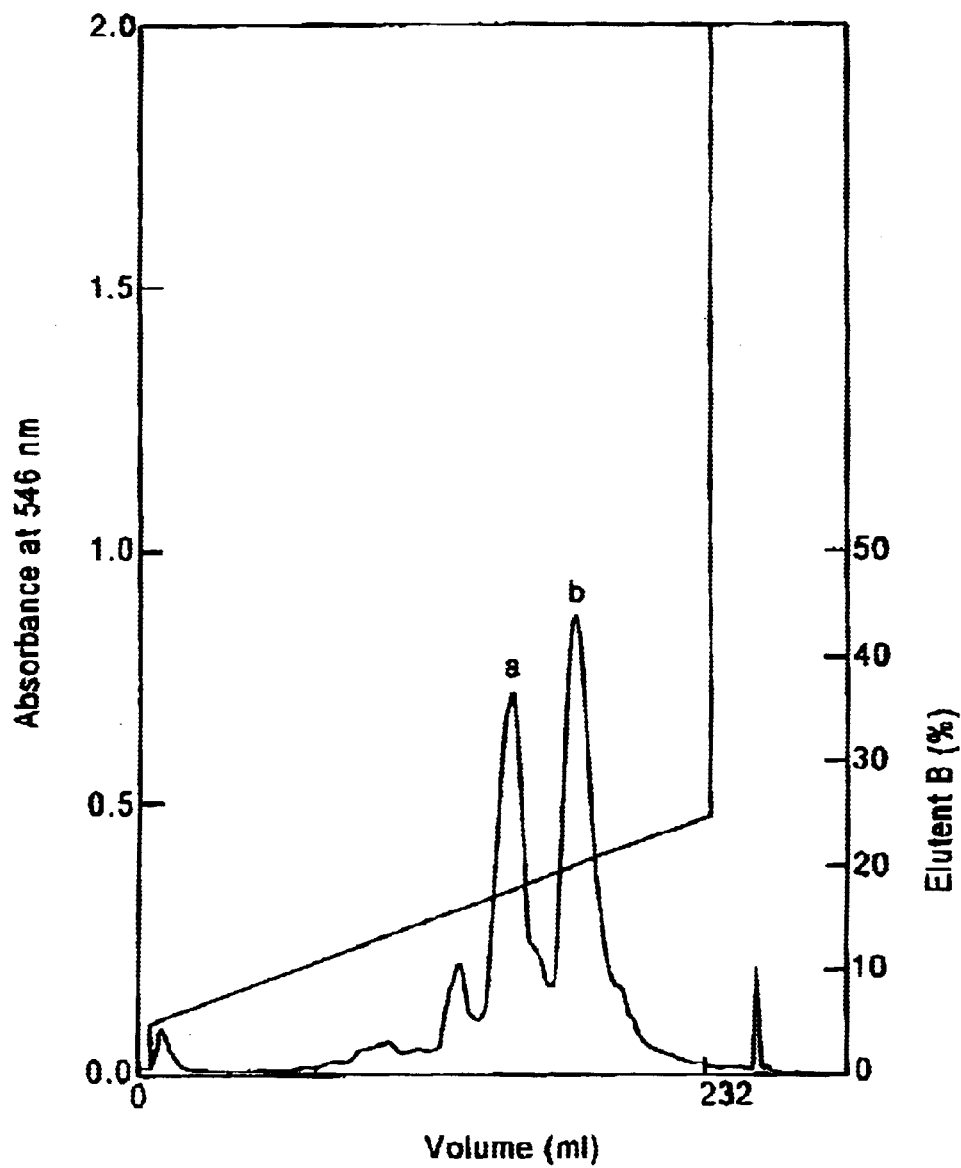
FIGS. 2A and 2B show the FPLC profiles of rHb (βN108Q) (peak b) (FIG. 2A) and rHb (βL105W) (peak b) (FIG. 2B).

As used herein, "Hb A" or "native Hb A" means human normal adult hemoglobin as obtained from human subjects.

"Recombinant human normal adult hemoglobin," "rHb A," and "unmodified rHb A" mean human normal adult hemoglobin produced through recombinant DNA technology and having essentially the same structure and function as native Hb A as described by Shen, et al. (1993), and U.S. Pat. No. 5,753,465.

"rHb (βL105W)" refers to a recombinant mutant human hemoglobin in which the leucine residue at position 105 of each of the β-chains of the Hb molecule has been replaced by a tryptophan residue. This hemoglobin possesses low oxygen affinity and high cooperativity in oxygen binding compared to Hb A. rHb (βL105W) is designed to form a hydrogen bond between α94Asp and β105Trp in the $\alpha_1\beta_2$ subunit interface in order to lower the oxygen affinity by stabilizing its deoxy quaternary structure.

"rHb (βN108Q)" refers to a mutant human hemoglobin produced through recombinant DNA technology in which the asparagine residue at position 108 of the β-chains located in the $\alpha_1\beta_1$ interface and in the central cavity of the Hb molecule, have been replaced by glutamine residues. This hemoglobin possesses low oxygen affinity, and high cooperativity in oxygen binding, and also increased resistance to autoxidation as compared to other known recombinant low oxygen affinity mutant hemoglobins, such as, rHb (αV96W) and rHb (αV96W, βN108K).

"Autoxidation" refers to the turning or conversion of oxyhemoglobin ("$HbO_2$" or "oxy-Hb") into methemoglobin ("met-Hb"). In $HbO_2$ the heme-iron atoms are in the reduced ferrous ($Fe^{2+}$) state, however, in met-Fib, the heme-iron atoms are in the oxidized ferric ($Fe^{3+}$) state.

"Deoxy" and "oxy" refer to the oxygenation state of the heme-iron atom in Hb A and rHbs. Oxyhemoglobin ("oxy-Hb" or "HbO2") has four oxygen molecules bound to the heme groups; deoxyhemoglobin ("deoxy-Hb") contains no oxygen molecules. In normal arterial blood, normal adult hemoglobin A ("Hb A") is in the oxy form ("Hb $O_2$ A" or "oxy-Hb A"). In venous blood, a portion of Hb A is in the deoxy form ("deoxy-Hb A").

"Carbonmonoxy-Hb," "HbCO A," "rHbCO," and "CO form" all refer to hemoglobin bound to carbon monoxide molecules rather than oxygen molecules.

"Ferri-hemoglobin," "ferri-Hb," "ferric form," "methemoglobin," "met-Hb", and "$Fe^{+3}$ state" all refer to hemoglobin with their respective heme-iron atoms oxidized to the ferric ($Fe^{3+}$) state. Ferri-Hb does not bind oxygen.

"Methionine aminopeptidase" refers to the enzyme methionine aminopeptidase which specifically cleaves the amino-(N) terminal methionine residue from a peptide sequence.

"Oxygen affinity" means the strength of binding of oxygen to a hemoglobin molecule. High oxygen affinity means hemoglobin does not readily release its bound oxygen molecules. The $P_{50}$ is a measure of oxygen affinity.

"Cooperativity" refers to the binding of oxygen by the four subunits of the hemoglobin molecule and is measured by the Hill coefficient ($n_{max}$). For Hb A in 0.1 M sodium phosphate at pH 7.4 and 29° C., $n_{max}$ is about 3.2.

The two classical quaternary structures are the T (tense) quaternary D structure for the low affinity deoxy-Hb and the R (relax) quaternary structure for the high affinity oxy-Hb. "R-type" or "R-like," and similar terms refer to those hemoglobins which exhibit characteristic quaternary structural markers, such as the proton resonance at 10.7 ppm from DSS on $^1$H-NMR spectra. "T-type" or "T-like" and similar terms refer to those hemoglobins which exhibit characteristic T quaternary structures, such as the proton resonance at ~14.0 ppm from DSS on $^1$H-NMR spectra.

II. Methods and Results

Using the *Escherichia coil* expression system described by Shen, et al. (1993): U.S. Pat. No. 5,753,465; and Kim, et al. (1995), U.S. Pat. No. 5,843,888, new non-naturally occurring artificial recombinant hemoglobins ("rHbs") have been constructed, having low oxygen affinity while maintaining high cooperativity in oxygen binding. One of the rHbS, rHb (βN108Q) also exhibits increased resistance to autoxidation as compared to certain other known low oxygen affinity mutants. More particularly, the present invention is directed to: a recombinantly produced mutant of Hb A, denoted herein as rHb (βN108Q), in which the asparagine residues at position 108 of each of the β-chains (SEQ ID NO: 8), located in the $\alpha_1\beta_1$ subunit interface and in the central cavity of the Hb molecule, have been replaced by glutamine residue; and a recombinantly produced mutant of Hb A, denoted herein as rHb (βL105W) in which the leucine residues at position 105 of each of the β chains (SEQ ID NO: 8) have been replaced by tryptophan and in this molecule a new hydrogen bond is formed from β105Trp to β94Asp in the $\alpha_1\beta_2$ subunit interface in order to lower the oxygen binding affinity by stabilizing its deoxy quaternary structure.

These new artificial hemoglobins, i.e., derived entirely from sources other than blood, possess a low oxygen affinity and high cooperativity in oxygen binding. Additionally, rHb (βN108Q) exhibits increased resistance to autoxidation as compared to other known low oxygen affinity mutants, such as rHb (αV96W) and rHb (αV96W, βN108K). Further, these new artificial hemoglobins exhibit no unused subunit disassociation when ligated. In a cell-free environment the rHbs of the present invention have similar or lower oxygen binding properties to those of Hb A in red blood cells. Such rHbs therefore are of value as hemoglobin-based oxygen carriers, i.e., potential blood substitutes, or hemoglobin therapeutics.

It is also within the scope of the present invention to prepare and use other low oxygen affinity hemoglobins with other appropriate mutations. In particular, the methods of the present invention may be used to produce other mutant hemoglobins with additional advantageous properties. Methods for evaluating the suitability of other useful mutants possessing the properties of such low oxygen affinity, high cooperativity, and increased resistance to autoxidation for use in a blood substitute or therapy are described herein below. The preferred materials and methods for obtaining rHb (βL105W) and rHb (βN108Q) are given in the following reference examples. While the rHbs of the present invention are preferably produced recombinantly, it is understood that non-recombinant methods may also be used.

The preferred mutant rHbs of the present invention, rHb (βL105W) and rHb (βN108Q), can switch from the R quaternary structure to the T quaternary structure in their ligated state upon the addition of an allosteric effector, IHP, and/or by lowering the temperature. The recombinant hemoglobins of the present invention can therefore be used to gain new insight regarding the nature of subunit interactions in the $\alpha_1\beta_2$ and $\alpha_1\beta_1$ interfaces and the molecular basis for the allosteric mechanism of hemoglobin.

As will be shown below, rHb (βN108Q) of the present invention shows a low oxygen affinity, an enhanced Bohr effect, but a similar cooperativity as that of Hb A, and also exhibits slower autoxidation to methemoglobin ("met-Hb") as compared to other known low oxygen affinity recombinant hemoglobins such as, for example, rHb ($\alpha$96Val→Trp) and rHb ($\alpha$96Val→Trp, β108Asn→Lys) (Kim, H. -W., et al. *Biochemistry* 35:6620–6627 (1996) (hereinafter "Kim, et al. (1996)"); Ho, C., et al. *Blood Substitutes: Present and Future Perspectives of Blood Substitutes* (Tsuchida, E., Ed.), Elsevier Science SA, Lausanne, Switzerland, pp. 281–296 (1998) (hereinafter "Ho, et al. (1998)"); Jeong, et al. (1999); and Tsai, et al. (1999), the disclosures of which are incorporated herein by reference), oxidize much faster. Therefore, rHb (βN108Q) can be useful for hemoglobin-based oxygen carriers and hemoglobin therapeutics.

Proton nuclear magnetic resonance ("$^1$H-NMR") studies show that rHb (βN108Q) has similar tertiary structure around the heme pockets and quaternary structure in the $\alpha_1\beta_1$ and $\alpha_1\beta_2$ subunit interfaces as compared to those of Hb A. $^1$H-NMR studies also demonstrate that rHb (βN108Q) can switch from the R quaternary structure to the T quaternary structure without changing its ligation state upon the addition of an allosteric effector, IHP, and/or by lowering the temperature. This suggests that the T quaternary structure of rHb (βN108Q) is more stable than that of Hb A. This is consistent with the molecular mechanism of low-oxygen affinity found in rHb ($\alpha$V96W) (Kim, H. -W., et al., *J. Mol. Biol.* 248:867 (1995) (hereinafter "Kin, et al. (1995)"); U.S. Pat. No. 5,843,888 and rHb ($\alpha$V96W, βN108Q) (Ho, et al. (1998); Tsai, et al. (1999)).

It has been reported by Carver, T. E., et al. *J. Biol. Chem.* 267: 14443 (1992); Brantley, R. E. Jr., et al. *J. Biol. Chem.* 268: 6995 (1993) (hereinafter "Brantley, et al. (1993)"; and Eich, R. F., et al. *Biochemistry* 35: 6976 (1996), the disclosures of which are incorporated herein by reference, that substitution of the Leu residue for phenylalanine at the B10 position can inhibit autoxidation in myoglobin and that at the B10 position of the $\alpha$-chain can lower NO reaction with deoxy- and oxy-Hb A. Reduction of the NO reaction with oxy-Hb A by appropriate mutations, i.e., $\alpha$L29F, in the distal heme pocket has been associated with reduction of the hypertensive effect recorded in vivo (Doherty, D. H., et al. *Nature Biotech.* 16: 672 (1998), the disclosure of which is incorporated herein by reference). Hence, as detailed below, such mutation was further introduced into βN108Q to produce a double mutant, rHb ($\alpha$L29F, βN108Q). It was found that this double mutant is more stable against autoxidation as compared to rHb (βN108Q), but exhibits comparable oxygen binding properties to those of Hb A in the presence of allosteric effector, 2 mM 2,3-BPG.

Mutant rHb (βL105W) was designed to form a new hydrogen bond from β105Trp to $\alpha$94Asp in the $\alpha_1\beta_2$ subunit interface in order to lower the oxygen binding affinity by stabilizing its deoxy quaternary structure. It was found that rHb (βL105W) possesses a very low oxygen affinity and maintains high cooperativity ($P_{50}$=28.2 mm Hg, $n_{max}$=2.6 in 0.1 M sodium phosphate at pH 7.4 and 29° C.) as compared to Hb A ($P_{50}$=9.9 mm Hg, $n_{max}$=3.2 in 0.1 M sodium phosphate at pH 7.4 and 29° C.). Mutant rHb ($\alpha$D94A, βL105W) and rHb ($\alpha$D94A) were designed to provide evidence that rHb (βL105W) forms a new hydrogen bond from β105Trp to $\alpha$94Asp in the $\alpha_1\beta_2$ subunit interface of the deoxy quaternary structure. The multinuclear, multidimensional nuclear magnetic resonance ("NMR") studies performed in accordance with the present invention in $^{15}$N-labeled rHb (βL105W) have identified the resonance of the indole nitrogen-attached proton of β105Trp for rHb (βL105W). $^1$H-NMR studies on Hb A and mutant rHbs were used to investigate the structural basis for the low oxygen affinity of rHb (βL105W). NMR results show that rHb (βL105W) forms a new hydrogen bond from β105Trp to $\alpha$94Asp in the $\alpha_1\beta_2$ subunit of the deoxy quaternary structure. It is believed that the low oxygen affinity of rHb (βL105W) is due to the formation of a new hydrogen bond between β105Trp and $\alpha$94Asp in the deoxy quaternary structure.

Proton nuclear magnetic resonance ("NMR") spectroscopy was used to study the tertiary and quaternary structures of Hbs in solution (Ho, et al. (1992)). Several exchangeable proton resonances at ~15 to ~9 ppm from the methyl proton resonance of 2,2-dimethyl-2-silapentane-5-sulfonate ("DSS") have been characterized as intersubunit H-bonds in the $\alpha_1\beta_1$ and $\alpha_1\beta_2$ subunit interfaces in both oxy and deoxy states of Hb A. These H-bonded protons observed by NMR can be used as structural markers in functional studies. In particular, the resonance at ~14 ppm from DSS has been identified as the inter-subunit H-bond between $\alpha$42Tyr and β99Asp in the $\alpha_1\beta_2$ interface of deoxy-Hb A, a characteristic feature of the T-structure of Hb A (Fung, L. W. -M., et al. *Biochemistry* 14:2526 (1975) (hereinafter "Fung, et al. (1975)"), 1975; Russu, I. M., et al. *Biochem. Biophys. Acta* 914:40 (1987) (hereinafter "Russu, et al. (1987)"). By observing this T-structure marker in both the deoxy and the CO forms of Hbs under various conditions, the stability of the T-conformation can be assessed and the transition from the T- to the R-structure can be monitored.

In the present invention, the strategy for designing rHbs with low oxygen affinity and high cooperativity was to stabilize the T-structure while not perturbing the R-structure. (See, Ho, et al. (1998); Tsai, et al. (1999)). This strategy has been demonstrated in the design of rHb ($\alpha$V96W), which has low oxygen affinity and normal cooperativity (Kim et al. (1995); U.S. Pat. No. 5,843,888). This designed mutation is located at the $\alpha_1\beta_2$ subunit interface and in the central cavity of the Hb molecule. According to $^1$H-NMR studies, rHbCO ($\alpha$V96W) can switch from the R-structure to the T-structure without changing its ligation state when the temperature is lowered and/or when IHP, an allosteric effector, is added. The crystal structure of rHb ($\alpha$V96W) in its T-state has shown a novel water-mediated H-bond between α96Trp $N_{\epsilon 1}$ and β101Glu $O\epsilon_2$ in the $\alpha_1\beta_2$ subunit interface (Puius, T. A., et al. *Biochemistry* 37: 9258 (1998) (hereinafter "Puius", et al. (1998)"). Both $^1$H-NMR studies and the crystal structure indicate that the T-structure of this rHb is stabilized. In the present invention, the NMR studies have also shown that rHbCO (βN108Q) and rHbCO (βN105W) can switch to the T quaternary structure even when they are still ligated. These results suggest that the T structure of these two rHbs are more stable than that of Hb A.

As stated above, the methods of the present invention may also be used to produce other mutant artificial hemoglobins with different properties as well as hemoglobins with mutations that compensate for mutants that are naturally occurring. The preferred materials and methods for obtaining rHb (βN108Q) and rHb (βL105W) are given in the following reference example. Non-recombinant methods may also be used.

REFERENCE EXAMPLE

Construction of Expression Plasmids for rHb (βN108Q) and rHb (βL105W)

The *E. coli* Hb A expression plasmids pHE2 and pHE7, which respectively contain human α- and β-globin genes and cDNAs, were used as the starting plasmids for expressing the mutant hemoglobins of the present invention. The construction of plasmids pHE2 and pHE7 and properties of the rHb A produced thereby are fully described in Shen, et al. (1993), U.S. Pat. No. 5,753,465, and Shen, T. -J., et al. *Protein Eng.* 10: 1085 (1997) (hereinafter "Shen, et al. (1997)"), Kim, et al. (1994), and U.S. Pat. No. 5,843,888), the disclosure of which is incorporated herein by reference.

The construction of plasmid pHE2009 for expression of mutant r Hb (βN108Q) using synthetic globin genes was carried out as follows. The plasmid pHE2 was used as the starting plasmid and an oligonucleotide of sequence 5'-CGTCTGCTGGGTCAGGTACTAGTTTGCG-3' (SEQ ID NO: 1) (mutated codon is underlined) was purchased from DNA International, Inc. (Lake Oswego, Oreg.) and used as a primer to introduce the mutation βN108Q into pHE2. Techniques for oligonucleotide synthesis are well known and this invention is not limited to any particular technique. The site-directed mutagenesis procedure followed the protocol of an "Altered Sites II In-Vitro Mutagenesis System" kit (Promega Corporation, Madison, Wis.) and the resultant plasmid pHE2009 contained the expected mutation βN108Q.

The construction of plasmids pHE2020 (mutant rHb (αD94A) and pHE2004 (mutant rHb βL105W)) using synthetic globin genes was similar to that of pHE2009, except the mutation oligonucleotide 5'-CTGCGTGTT GCTCCGGTCAACTTCAAACTG-3' (SEQ ID NO: 2), mutated codon αD94A is underlined) and 5'-GGAAAACTTCCGA TGGCTGGGTAACGTAC-3' (SEQ ID NO: 3, mutated codon βL105W is underlined) were used. Both oligonucleotides were purchased from DNA International, Inc. (Lake Oswego, Oreg.).

The construction of plasmid pHE2017 (mutant rHb (αD94A, βL105W)) was accomplished by ligating the 0.51-kb SmaI-PstI fragment of pHE2020 with the 6.34-kb kb PstI-SmaI fragment of pHE2004. The construction of plasmid pHE2018 for expression of mutant rHb (αL29F, βN108Q) was accomplished by ligating the 6.06-kb PstI-BamHI fragment of pHE2009 with the 0.79-kb BamHI-PstI fragment of pHE284.

The construction of plasmid pHE7009 for expression of mutant rHb (βN108Q) using the human globin cDNAs was carried out as follows. The coding sequences of human α- and β-globin cDNAs in plasmid pHE7 were inserted into pTZ18U (Bio-Rad Laboratories, Hercules, Calif.) by methods well known in the art. Site-directed mutagenesis was performed as described by Kunkel, T. M. et al., *Proc. Natl. Acad. Sci. USA* 82:408 (1985) the disclosures of which are incorporated herein by reference, and Shen, et al. (1993). An oligonucleotide of sequence 5'-ACAGACCAGTA CTTGTCCCAGGAGCCT-3' (SEQ ID NO: 4) (mutated codon Asn→Gln is underlined) was purchased from DNA International, Inc. (Lake Oswego, Oreg.), and used as the mutation primer. The human normal β-globin cDNA in plasmid pHE7 was then replaced with the mutated cdNA to produce plasmid pHE7009. The DNA sequences for the α- and β-globin cDNAs in pHE7009 are shown in FIG. 1A (SEQ ID NO: 5). The amino acid sequence for the human beta chains of hemoglobin is shown in SEQ ID NO; 8. Plasmid pHE7009 in host cell *E. coli* JM109 and designated pHE7009/JM109 was deposited with the American Type Culture Collection of Manassas, Va. on Apr. 27, 2000 under number PTA-1768.

The construction of plasmid pHE7004 for expression of mutant rHb (βL105W) using the human globin cDNAs was carried out in the similar way as that of plasmid pHE7009, except an oligonucleotide of sequence 5'-CCTGA GAACTTCAGGTGGCTAGGCAACGTGCTGGTC-3' ((SEQ ID NO: 6), mutated codon Leu→Trp is underlined) was purchased from DNA International, Inc. (Lake Oswego, Oreg.) and used am the mutation primer. The DNA sequences of the α- and β-globin cDNAs in pHE7004 are shown in FIG. 1B (SEQ ID NO: 7). The amino acid sequence for the human beta chains of hemoglobin is shown in SEQ ID NO:8. Plasmid pHE7004 in host cell *E. coli* JM109 and designated pHE7004/JM109 was deposited with the American Type Culture Collection of Manassas, Va. on Apr. 27, 2000 under number PTA-1769.

Plasmids pHE7009, and pHE7004 were individually transformed in *E. coli* strain JM109 (Promega, Madison, Wis.) by methods well known in the art. *E. coli* cells were grown in Terrific Broth ("TB") medium plus 100 μg/mL ampicillin in a 10-liter Microferm fermenter (New Brunswick Scientific, Model BioFlo 3000) at 32° C. until the optical density at 600 nm reached 10. TB medium contains 1.2% bactotryptone, 2.4% bactoyeast extract, 0.17M $K_2HPO_4$, 0.072M $K_2HPO_4$, and 1% glucose solution. Expression of rHbs was induced by adding isopropyl β-thiogalactopyranoside (Sigma, St. Louis, Mo.) to a concentration of 0.1–0.4 mM. The culture was then supplemented with hemin (20–50 mg/liter) (Sigma) and the growth was continued for at least another 4 hr. The cells were harvested by centrifugation and stored frozen at −80° C. until needed for purification. For details, refer to Shen, et al. (1993), and Shen, et al. (1997).

Although *E. coli* cells are presently preferred for expressing and producing the recombinant mutant hemoglobin of the present invention, the invention is not limited to *E. coli* cells. Other appropriate expression systems such as yeast, insect cells and transgenic animals such as pigs, sheep, and cows may also advantageously be used to express mutant hemoglobins. Plasmids pHE7009 and pHE7004 have been optimized for *E. coli* cells, but other expression systems may be advantageously used. The plasmids can also be constructed with human genes.

Isolation and Purification of rHbs

Figure 2B:
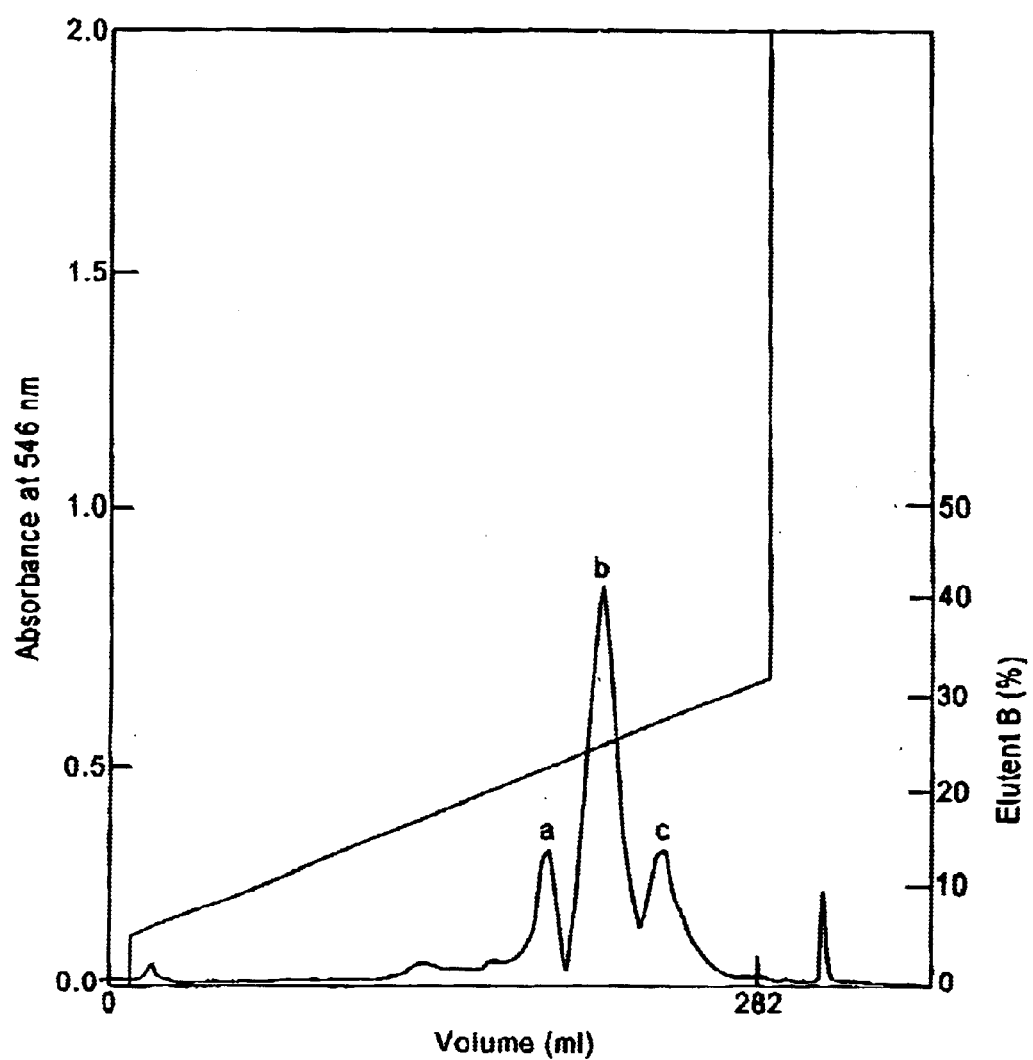

The recombinant hemoglobins obtained from cells transformed with plasmids pHE7009 and pHE7004 were purified as essentially described by Shen, et al. (1993), and Shen, et al. (1997). The frozen stored cell paste was put into lysis buffer (40 mM trisbase/1 mM benzamidine) (Sigma) at 3 ml/gm of cell paste). The cell lysis procedure was used to pass the cell paste through a high-pressure homogenizer (Model EmulsiFlex-C5, Avestin) 3 times. The lysate was then centrifuged at 4° C. for 2.5 hours at 13,000 rpm in a Beckman centrifuge (Beckman JA14 rotor). The supernatant from the lysate was saturated with CO gas and left at 30° C. overnight as described by Tsai, et al. (1999). The supernatant was then put through a Millipore Minitan Acrylic Ultrafiltration system to concentrate the protein. Polyethyleneimine (Sigma) was added to a final concentration of 0.5% to precipitate nucleic acids. After centrifugation, the sample was dialyzed against 20 mM Tris-HCl/0.5 mM triethylenetetraamine ("TETA") (Sigma) at pH 8.3 overnight with one or two changes of buffer. Throughout the above procedures, the sample was kept at 4° C. and maintained in a CO atmosphere. Following the procedures of Shen, et al. (1993) and Shen, et al. (1997), the rHb fraction collected after passage through a Q-Sepharose Fast-Flow column (Pharmacia Anion Exchanger) Pharmacia was oxidized and reduced, and converted to the CO form. This Hb solution was then purified by eluting through a fast protein liquid chromatography ("FPLC") Mono-S column (Pharmacia Cation Exchanger, HR 16/10) with a gradient of 10 mM sodium phosphate in 0.1–0.5 mM ethylenediaminetetraacetic acid ("EDTA") at pH 6.8 (eluent A) and 20 mM sodium phosphate in 0.1–0.5 mM EDTA at pH 8.3 (eluent B).

rHb (βN108Q) was eluted individually in two major peaks. FIG. 2A shows peak a and peak b for rHb (βN108Q). FIG. 2B shows rHb (βL105W) was eluted individually in three major peaks, peaks a, b, and c. rHbs collected from peak b in both cases contained less than 2% methionine at the amino-termini and with the correct molecular weight.

Mass Spectrometry

Hb samples subjected to mass spectrometry were dialyzed extensively against distilled $H_2O$ and then lyophilized. Immediately before analysis, the samples were dissolved in water to a concentration of 125 pmol of Hb per $\mu$l of $H_2O$ (7.8 mg/ml). Aliquots of these solutions were then diluted to give a final concentration of 10 pmol/$\mu$l of 50:50 water/acetonitrile containing 0.2% formic acid. Aliquots (10 $\mu$l) of these final solutions were introduced into the electrospray ion source at 5 $\mu$l/minute.

The electrospray ionization analyses were performed on a VG Quattro-BQ (Fisons Instruments, VG Biotech, Altrincham, U.K.), as described by Shen, et al. (1993). Automated cycles of Edman degradation were performed on an Applied Biosystems gas/liquid-phase sequencer (Model 470/900A) equipped with an on-line phenylthiohydantoin amino acid analyzer (Model 120A). These two analytical procedures were used to assess the quality of the rHbs. All rHbs used in this study had the correct molecular weights and contained less than 2% of methionine at the amino termini.

Oxygen-Binding Properties of rHbs

Oxygen dissociation curves of rHbs were measured by a Hemox-Analyzer (TCS Medical Products, Huntington Valley, Pa.) at 29° C. as a function of pH. The concentration of Hb used was approximately 0.1 mM per heme. The methemoglobin ("met-Hb") reductase system described by Hayashi, A., et al. *Biochem. Biophys. Acta* 310:309 (1973), the disclosure of which is incorporated herein by reference, was used if needed to reduce the amount of met-Hb in the sample. A visible absorption spectrum of each sample was recorded immediately after oxygen equilibrium measurement, and the met-Hb content was estimated by using the extinction coefficients of Hb reported by Antonini, E., *Physiol. Rev.* 45:123 (1965), the disclosure of which is incorporated herein by reference. Oxygen equilibrium parameters were derived by fitting Adair equations to each equilibrium oxygen-binding curve by a nonlinear least-squares procedures. $P_{50}$, a measure of oxygen affinity, was obtained at 50% saturation. The Hill coefficient ($n_{max}$), a measurement of cooperativity, was determined from the maximum slope of the Hill plot by linear regression. $n_{max}$ was derived between 60% and 65% oxygen saturation. The accuracy of $P_{50}$ measurements in mm Hg is ±5% and that for $n_{max}$ is ±7%.

$^1$H-NMR Spectroscopy Measurements of rHbs $^1$H-NMR spectra of rHbs were obtained on Bruker AVANCE DRX-300, AVANCE DRX-500, and AVANCE DRX-600 NMR spectrometers that were operated at 300, 500, and 600 MHz, respectively, and at temperatures ranging from 10° C.–36° C. All of the Hb samples were placed in 0.1 M sodium phosphate buffer (in 100% $H_2O$) at pH 7.0. The Hb concentration range was approximately 5% (~3 mM in terms of heme). The water signal was suppressed by using the "jump-and-return" pulse sequence as reported by Plateau, P., et al. *J. Am. Chem. Soc.* 104:7310 (1982) (hereinafter "Plateau, et al. (1982)"), the disclosure of which is incorporated herein by reference. Proton chemical shifts are referenced to the methyl proton resonance of the sodium salt of 2,2-dimethyl-2-silapentane-5 sulfonate ("DSS") indirectly by using the water signal, which signal occurs at 4.76 ppm downfield from that of DSS at 29° C., as the internal reference.

Autoxidation of rHbs

The autoxidation of rHbs was recorded by monitoring the disappearing rate of the oxy-marker (−2.34 ppm from DSS) from Bruker AVANCE DRX-300 $^1$H-NMR spectra. The autoxidation reaction was carried out in PlasmaLyte buffer (Baxter) (5% $D_2O$) with 5 mM EDTA at pH 7.4 and at 37° C. The $HbO_2$ concentration was 5% (~3 mM in terms of heme).

Functional Studies

Oxygen-binding Properties of rHbs

Figure 3A:
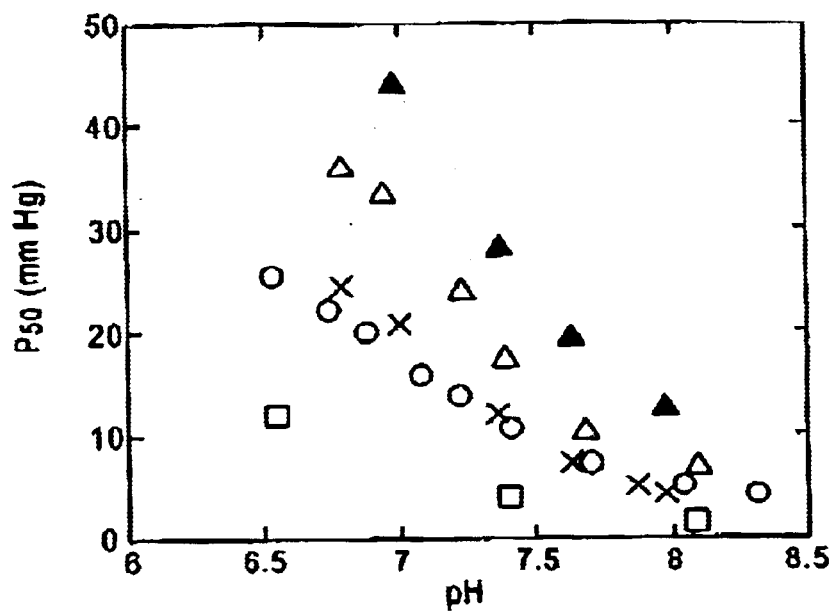
FIGS. 3A and 3B show the pH dependence of the oxygen affinity ($P_{50}$) and the Hill coefficient ($n_{max}$), respectively, of rHb (αL29F) (□); rHb (βN108Q) (△); rHb (αL29F, βN108Q) (X); rHb (βL105W) (▲); and Hb A (○) in 0.1 M sodium phosphate buffer at 29° C. Oxygen dissociation data were obtained with 0.1 mM Hb.
Figure 3B:
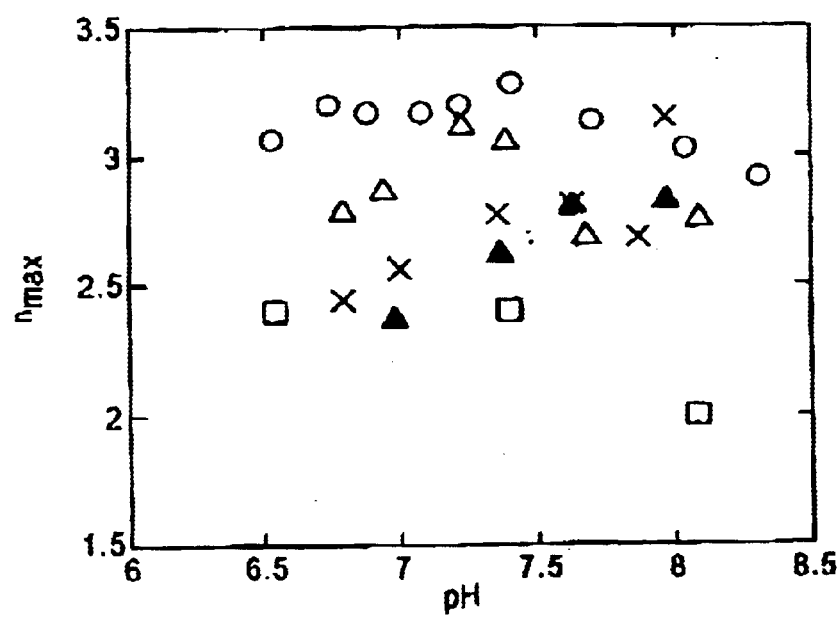

FIGS. 3A and 3B show the oxygen-binding measurements of rHb (αL29F), rHb (βN108Q), rHb (α29F, βN108Q), rHb (βL105W), and Hb A in 0.1 M sodium phosphate buffer as a function of pH at 29° C. rHb (βN108Q) exhibits a significantly lower oxygen affinity as compared to that of Hb A over the pH range from pH 6.79 to pH 8.09. The oxygenation process of rHb (βN108Q) is very cooperative with an $n_{max}$ value of about 2.7 to 3.1 depending on the pH, compared to about 3.2 for Hb A (FIG. 3B). On the other hand, the mutation at the α-chain B10 position, i.e., αL29F, increases the oxygen affinity and decreases the cooperativity. rHb (αL29F, βN108Q) shows slightly higher $P_{50}$ values as compared to those of Hb A at pH<7.4, suggesting that the effect of the mutations on the oxygen affinity is additive. rHb (αL29F, βN108Q) preserves cooperativity in binding of oxygen with an $n_{max}$ value of 2.4 to 2.8 (FIG. 3B). rHb (βL105W) exhibits very low oxygen affinity (about 2–3 times lower) and maintains normal cooperativity from pH 7.0 to 8.0 as compared to Hb A.

Figure 4:
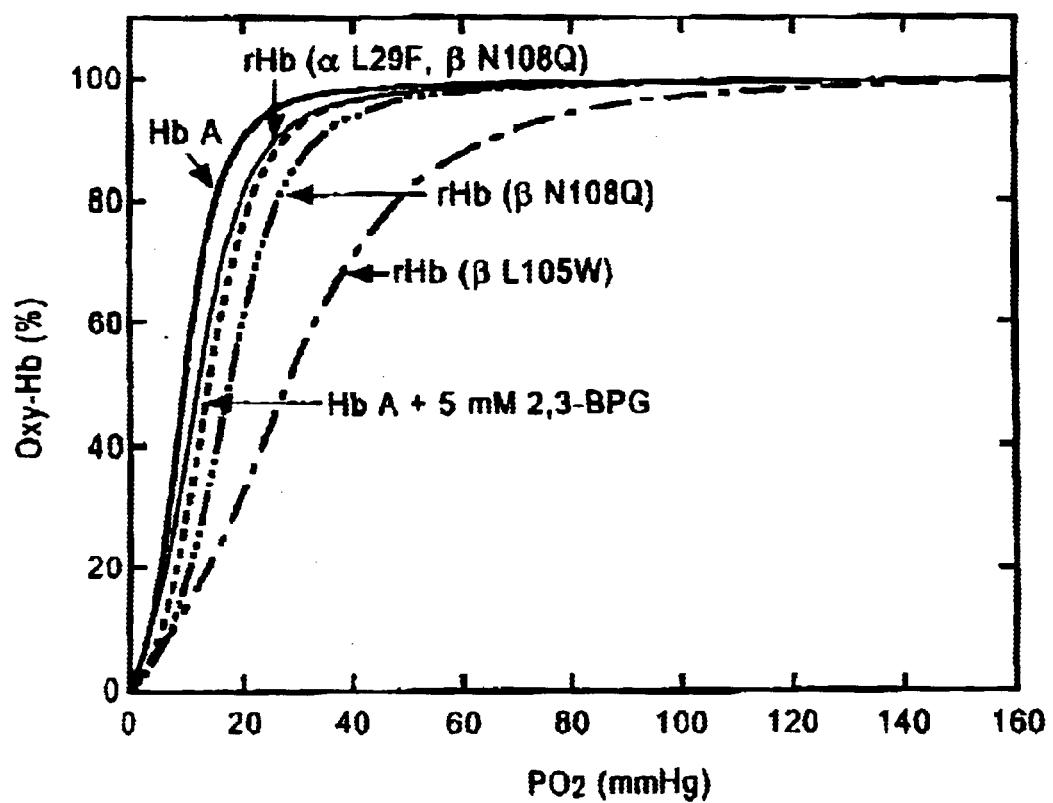
FIG. 4 shows oxygen-binding curves of rHb (βN08Q); rHb (αL29F, βN108Q); rHb (βL105W); and Hb A with and without the presence of allosteric effector, 5 mM 2,3-BPG, in 0.1 M phosphate buffer at pH 7.4 and 29° C. Protein concentration was 0.1 mM heme.

FIG. 4 shows that the oxygen affinities of rHb (βN108Q) and also rHb (βL105W) measured in the absence of 2,3-BPG are lower than that of Hb A in the presence of 5 mM 2,3-BPG, making them potential candidates for an oxygen carrier in a blood substitute system. FIGS. 3A and 3B also show that the alkaline Bohr effect (which, in Hb A, results in a decrease in oxygen affinity with a lowering of the pH)

is enhanced in rHb (βN108Q) and rHb (αL29F, βN108Q) compared to Hb A.

Table 1 below compares the number of Bohr protons released upon oxygenation per heme calculated from the linkage equation $AH^+ = -\partial \log P_{50}/\partial pH$. (Wyman, J., *Adv. Protein Chem.* 4:407 (1948) and *Adv. Protein Chem.* 19:233 (1964), (hereinafter "Wyman, J. (1948) and (1964)") the disclosures of which are incorporated herein by reference. Both rHb (βN108Q) and rHb (αL29F, βN108Q) release more Bohr protons than Hb A.

TABLE 1

Bohr effect of Hb A, rHb (βN108Q), rHb (αL29F, βN108Q), and rHb (βL105W) in 0.1 M sodium phosphate buffer at 29° C.

| Hemoglobin | $\partial \log P_{50}/\partial pH$ in 0.1 phosphate |
|---|---|
| Hb A | 0.48 (pH 6.79–8.00) |
| rHb (βN108Q) | 0.56 (pH 6.79–8.09) |
| rHb (αL29F, βN108Q) | 0.67 PpH 6.79–7.97) |
| rHb (βL105W) | 0.55 (pH 7.00–8.00) |

Autoxidation.

Figure 5:
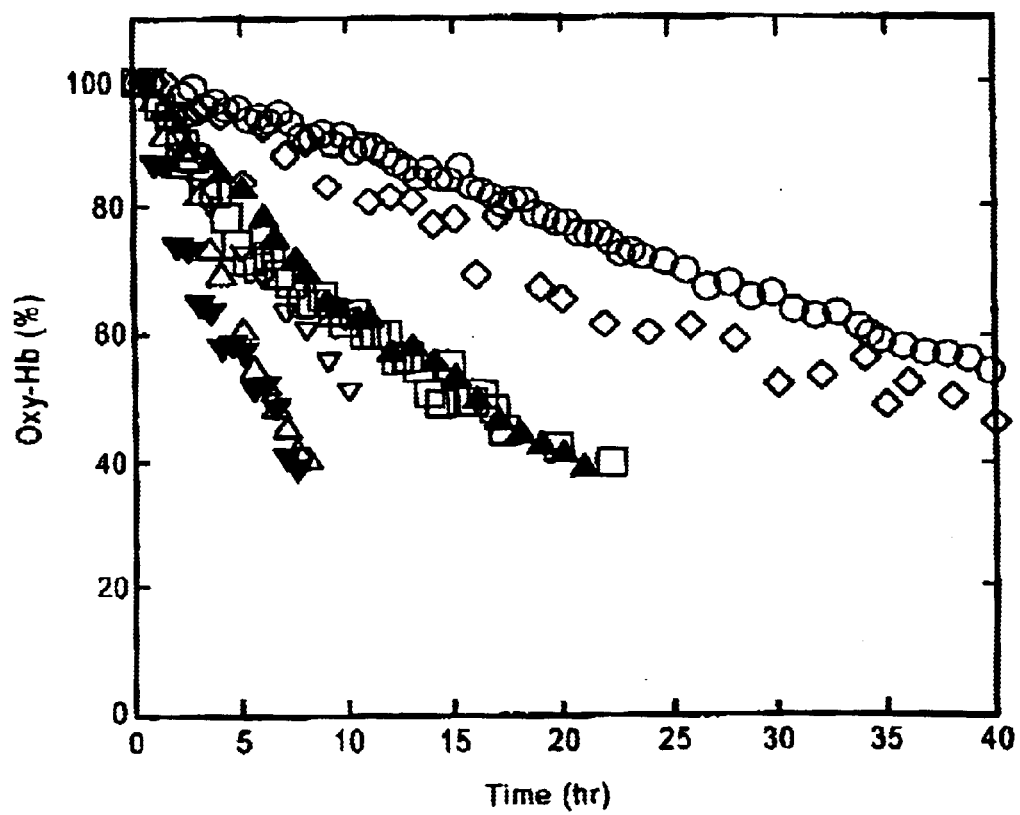
FIG. 5 shows the autoxidation of Hb A (○); rHb (βN108Q) (▲); rHb (βL105W) (△); rHb (αV96W) (▽); rHb (αV96W, βN108K) (▼); rHb (αL29F, βN108Q) (◇); and rHb (αL29F, αV96W, βN108K) (□) in PlasmaLyte buffer in the presence of 5 mM EDTA and 5% $D_2O$ at pH 7.4 and 37° C., The autoxidation process was measured by monitoring the rate of disappearance of the oxy-marker at −2.34 ppm upfield from DSS by 300-MHz $^1$H-NMR.

The autoxidation process was monitored for oxy-Hb A, oxy-rHb (βN108Q), oxy-rHb (αL29F, βN108Q), oxy-rHb (βL105W) and three other known low-oxygen affinity mutants, oxy-rHb (αV96W), oxy-rHb (αV96W, βN108K) and oxy-rHb (αL29F, αV96W, βN108K), by a 300-MHz NMR spectrometer. The resonance at −2.34 ppm upfield from DSS has been assigned to the $\gamma_2 CH_3$ of E11Val of Hb A in the oxy form of Hb A (Dalvit, C., et al., *Biochemistry* 24:3398 (1985), the disclosure of which is incorporated herein by reference). Monitoring the rate of disappearance of the oxy-marker (−2.34 ppm from DSS) as a function of time allows for the determination of the autoxidation rate of the Hb samples. The results are shown in FIG. 5. The percentage of ferrous-Hb varies with time (t) mono-exponentially and the autoxidation rate constant can be obtained from: $[\text{ferrous-Hb}]_t = [\text{ferrous-b}]_{t=0} \times \exp(-k_{auto} \times t)$, where $k_{auto}$ is the autoxidation rate constant. The autoxidation rate constants of Hb A and r Hbs are listed in Table 2 below. At pH 7.4 and 37° C. in PlasmaLyte buffer, rHb (βN108Q), rHb (βL105W), rHb (αV96W), and rHb (αV96W, βN108K) autoxidized 2.8-, 8-, 4.4-, and 8-times faster than Hb A. rHb (βN108Q) is shown be to more stable against autoxidation than other known low-oxygen affinity mutants developed in the laboratory; i.e., rHb (αV96W), rHb (βL105W), and rHb (αV96W, βN108K). The autoxidation rate is slowed down by introducing the mutation αL29F into rHb (βN108Q) and rHb (αV96W, βN108K). rHb (αL29F, βN108Q) and rHb (αL29F, αV96W, βN108K) autoxidized 2.5-and 2.8-times slower than rHb (βN108Q) and rHb (αV96W, βN108K), respectively. Thus, the mutation αL29F is very effective in slowing down the autoxidation process as suggested by the results on myoglobin (Brantley, et al., (1993), the disclosure of which is incorporated herein by reference). Hemichrome-like spectra are observed in the autoxidation process of only rHb (αL29F, αV96W, βN108K) among all the low oxygen affinity rHbs studied. Hemichrome forms when methemoglobin (met-Hb) converts from the ferric high-spin form to the ferric low-spin form in which the distal imidazole displaces the $H_2O$ ligand (Levy et al., *Biochemistry* 29: 9311 (1990); Levy, et al., *Biophys. J.* 61: 750 (1992); Blumberg, et al., *Adv. Chem. Series* 100: 271 (1991)). This is in accordance with the results from Jeong et al. (1999) in which the oxidized form of rHb (αL29F, αV96W, βN108K) exhibits of hemichrome-like spectra, making it undesirable to be considered as a candidate for an oxygen carrier.

TABLE 2

Autoxidation rate constants, oxygen affinity and cooperativity of low-oxygen affinity mutants.

| Hemoglobin | $k_{auto}$ (h$^1$)[a] | $P_{50}$ (mm Hg)[b] | $n_{maxn}$[b] |
|---|---|---|---|
| Hb A | 0.0158 ± 0.0002 | 9.64 | 3.28 |
| rHb (βN108Q) | 0.0449 ± 0.0007 | 17.46 | 3.10 |
| rHb (αL29F, βN108Q) | 0.0181 ± 0.0006 | 12.06 | 2.77 |
| rHb (βL105W) | 0.123 ± 0.0048 | 28.2 | 2.60 |
| rHb (αV96W) | 0.0689 ± 0.0008 | 16.38 | 2.94 |
| rHb (αV96W, βN108K) | 0.125 ± 0.0051 | 50.65 | 2.36 |
| rHb (αL29F, αV96W, βN108K) | 0.0449 ± 0.0014 | 21.97[c] | 1.81[c] |

[a]Rate constants for the autoxidation (kauto) of Hb A and r Hbs are obtained at [oxy-Hb] 3 mM heme in PlasmaLyte buffer at pH 7.4 and 37° C.
[b]Oxygen affinity and cooperativity were obtained in 0.1 M sodium phosphate buffer at 29° C. and pH 7.4. Protein concentrations were 0.1 mM heme.
[c]From Jeong, et al. (1999).

Structural Studies of rHb (βN108Q) and rHb (αL29F, βN108K) $^1$H-NMR Investigations $^1$H-NMR spectroscopy is an excellent tool for monitoring changes in the tertiary and quaternary structures of Hb A and its variants (see, e.g., Shen, et al. (1993); Kim, et al. (1994); Kim, et al. (1995); Kim, et al. (1996); and Barrick, D., et al. *Nat. Struct. Biol.* 4:78 (1997), the disclosures of which are incorporated herein by reference). FIG. 6A shows the exchangeable proton resonances and FIG. 6B shows the ring-current-shifted resonances of Hb A, rHb (βN108Q), and rHb (αL29F, βN108Q) in the CO form measured at 500 MHz. The ring-current-shifted resonances are sensitive to the orientation and/or conformation of the heme group relative to the amino acid residues in the heme pockets, i.e., the tertiary structure of the Hb molecule (see Ho, C., *Adv. Protein Chem.* 43:153 (1992), (hereinafter "Ho (1992)"), the disclosure of which is incorporated herein by reference). The resonances at ≈−1.8 and ≈−1.7 ppm have been assigned to the $\gamma_2$-$CH_3$ of the E11Val of the β-chain and α-chain of HbCO A, respectively (Lindstrom et al. (1972); Dalvit et al. (1985)). These two resonances are not changed in rHbCO (βN108Q). However, the resonance assigned to the $\gamma_2$-$CH_3$ of the α-E11Val of rHbCO (αL29F, βN108Q) is shifted upfield to ≈−2.0 ppm, suggesting that the $\gamma_2$-$CH_3$ group of the α-E11 valine residues in rHbCO (αL29F, βN108Q) is located closer to the normal of the heme than in HbCO A. α29L is in close proximity to E11Val, hence, the amino acid substitution αL29F is expected to alter the conformation of the distal heme pocket site of the α-chain. There are some other changes in the ring-current-shifted resonances among these rHbs. The experience has been that minor differences in the intensity and positions of ring-current-shifted resonances are common features in many rHb mutants. (See, for example, Shen, et al. (1993); Kim, et al. (1994); Kim, et al. (1995); and Kim, et al. (1996); Ho, et al. (1998); Sun, D. P., et al. *Biochemistry* 36:6663 (1997) (hereinafter "Sun, et al. (1997)"), the disclosure of which is incorporated herein by reference; and Tsai, et al. (1999)). These changes reflect slight adjustments of the conformation of the hemes and/or the amino acid residues in the heme pockets as the result of the mutation.

The exchangeable proton resonances of the Hb molecule arise from the exchangeable protons in the subunit interfaces. Of special interest to the present invention are the exchangeable proton resonances at 14.2, 12.9, 12.1, 11.2, and 10.7 ppm from DSS, which have been characterized as the inter-subunit H-bonds in the $\alpha_1\beta_1$ and $\alpha_1\beta_2$ subunit interfaces in both deoxy (T) and/or oxy (R) states of Hb A (Russu, et al (1987); sung, et al. (1975)); and Ho (1992), the disclosures of which are incorporated herein by reference). The resonances at 12.9 ppm and 12.1 ppm from DSS have been assigned to the H-bonds between $\alpha$122His and $\beta$35Tyr, and $\alpha$103His and $\beta$131Gln, respectively (see Russu, et al. (1987) and Simplaceanu, et al. *Biophys. J.* 79:1146 (2000) (hereinafter "Simplaceanu, et al. (2000)"). In the spectra of rHbCO ($\beta$N108Q) and rHbCO $\alpha$L29F, $\beta$N108Q) (as seen in FIG. 6A), three resonances instead of one occur corresponding to the chemical shift of HbCO A at 12.1 ppm. The main peak occurs at 12.0 ppm, with a shoulder at 11.8 ppm and an extra resonance at 12.3 ppm. The intensities of the resonances at 12.3 and 11.8 ppm are not even $\frac{1}{10}$ of the ones at 12.0 ppm and at 12.9 ppm, indicating that these two extra resonances are unlikely to be contributed by additional protons. The sum of the integrated areas of the resonances at 11.8, 12.0, and 12.3 ppm is about the same as the area of the single resonance at 12.9 ppm, suggesting the coexistence of three conformers of rHb ($\beta$N108O) in Co form.

Figures 7A, 7B:
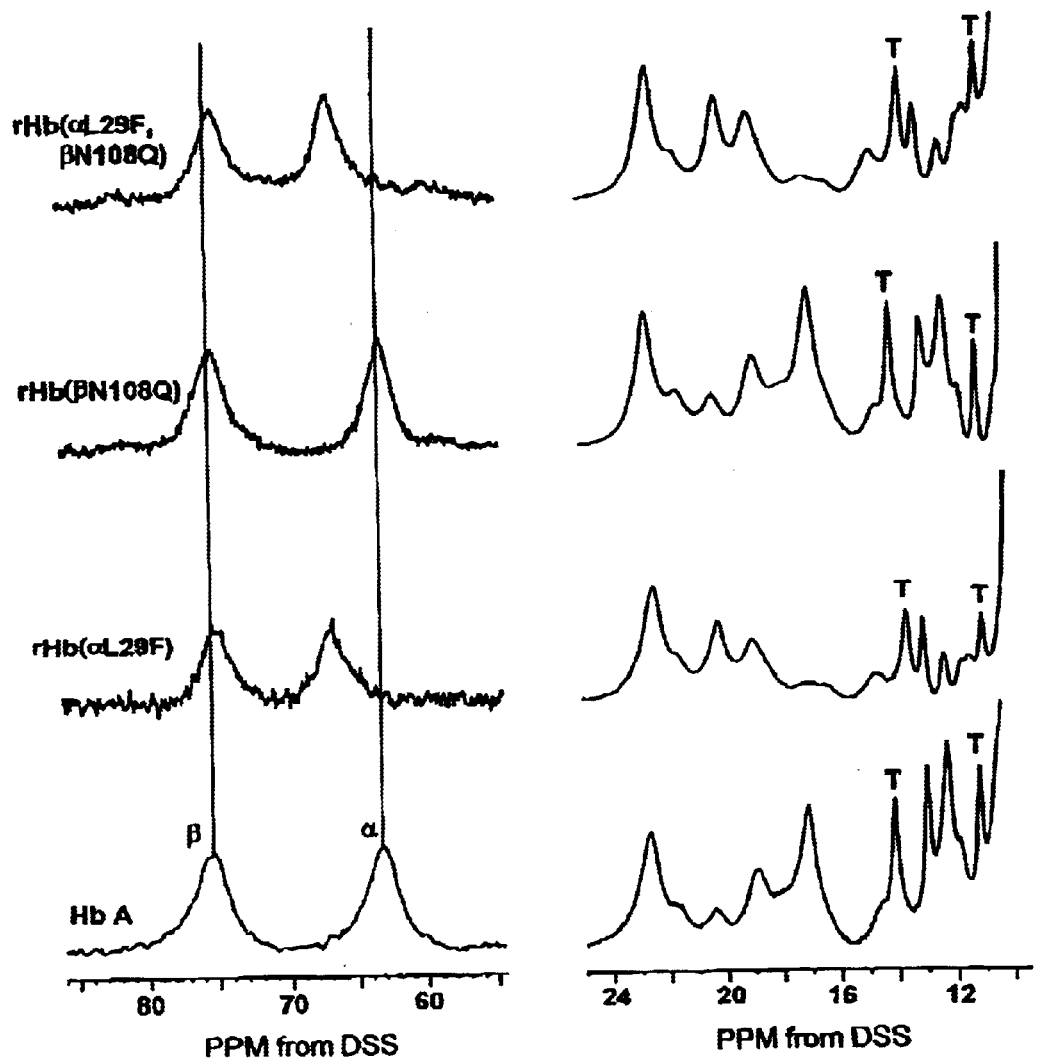
FIGS. 7A and 7B are 300-MHz $^1$H-NMR spectra showing ferrous hyperfine-shifted $N_δH$ resonances of proximinal histidines and hyperfine-shifted and exchangeable proton resonances, respectively, of rHb A; rHb (αL29F); rHb (βN108Q); and rHb (αL29W, βN108Q), all in the CO form, in 0.1 M sodium phosphate buffer at pH 7.0 and 29° C.

FIG. 7A shows the hyperfine-shifted and FIG. 7B shows the exchangeable proton resonances of rHbs and Hb A in the deoxy form in 0.1 M phosphate at pH 7.0 and 29° C. The resonance at 63 ppm from DDS has been assigned to the hyperfine-shifted $N_\delta$H-exchangeable proton of the proximal histidine residue ($\alpha$87His) of the $\alpha$-chain of deoxy-Hb A and the one at 77 ppm from DSS has been assigned to the corresponding residue of the 5-chain ($\beta$92His) of deoxy-Hb A (Takahashi, S., et al. *Biochemistry* 19:5196 (1980) and La Mar, G. N., et al. *Biochem. Biophys. Res. Commun.* 96:1172 (1980), the disclosures of which are incorporated herein by reference). The chemical shift positions of these two proximal histidyl resonances in rHb ($\beta$N108Q) are exactly the same as those of Hb A, indicating no perturbations around the proximal histidine residues of this rHb. However, the resonance at 63 ppm from DSS of rHb ($\alpha$L29F) and rHb ($\alpha$L29F, $\beta$N108Q) is shifted 4 ppm downfield to 67 ppm, reflecting a change in the environment of the proximal heme pocket of the $\alpha$-chain as a result of the mutation at $\alpha$L29F.

The spectral region from 10–25 ppm arises from the hyperfine-shifted resonances of the porphyrin ring and the amino acid residues situated in the proximity of the heme pockets and the exchangeable proton resonances. There are no noticeable differences seen in the resonances from 10–25 ppm between deoxy-Hb A and deoxy-rHb ($\beta$N108Q). However, there are spectral changes in rHb ($\alpha$L29F) and rHb ($\alpha$L29F, $\beta$N08Q) over the region from 16–20 ppm, reflecting changes in the environment of the heme pockets of both the $\alpha$- and the $\beta$-chains. The resonance at 14.2 ppm has been identified as the inter-subunit H-bond between $\alpha$42Tyr and $\beta$99Asp in the $\alpha_1\beta_2$ interface in deoxy-Hb A (Fung, et al. (1975)), a characteristic feature of the deoxy (T) quaternary structure of Hb A (Perutz, (1970)). This resonance of rHb ($\alpha$L29F) and rHb ($\alpha$L29F, $\beta$N108Q) is shifted 0.5 ppm upfield to 13.7 ppm, indicating that this $\alpha_1\beta_2$ interface H-bond in the deoxy form is perturbed by the mutation at $\alpha$L29F.

Figure 8A:
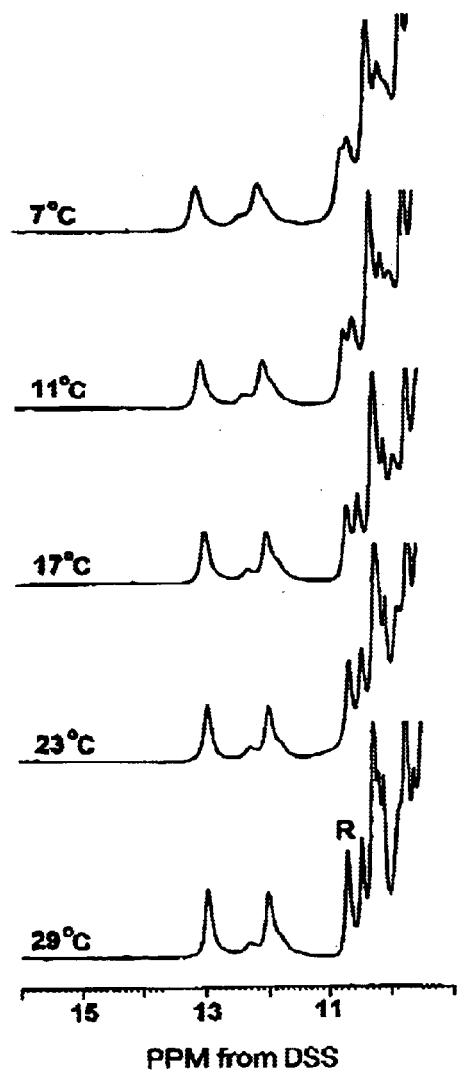
FIGS. 8A and 8B are 500-MHz spectra showing the exchangeable proton resonances of rHb (βN108Q) in the CO form in 0.1 M sodium phosphate buffer at pH 7.0 at 500 MHz at various temperatures (7° C., 11° C., 17° C., 23° C., 29° C.), without an allosteric effector (FIG. 8A) and with 4 mM inositol hexaphosphate ("IHP") (FIG. 8B).
Figure 8B:
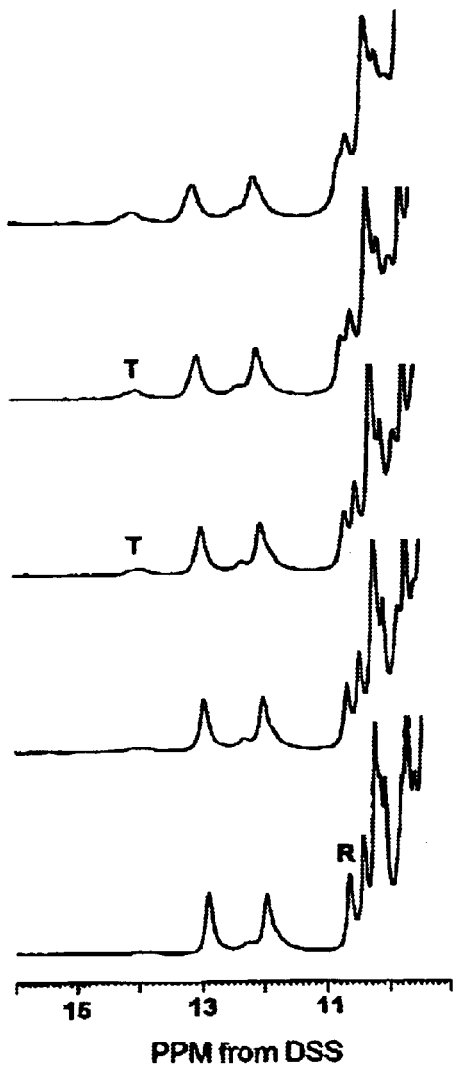
Figure 9A:
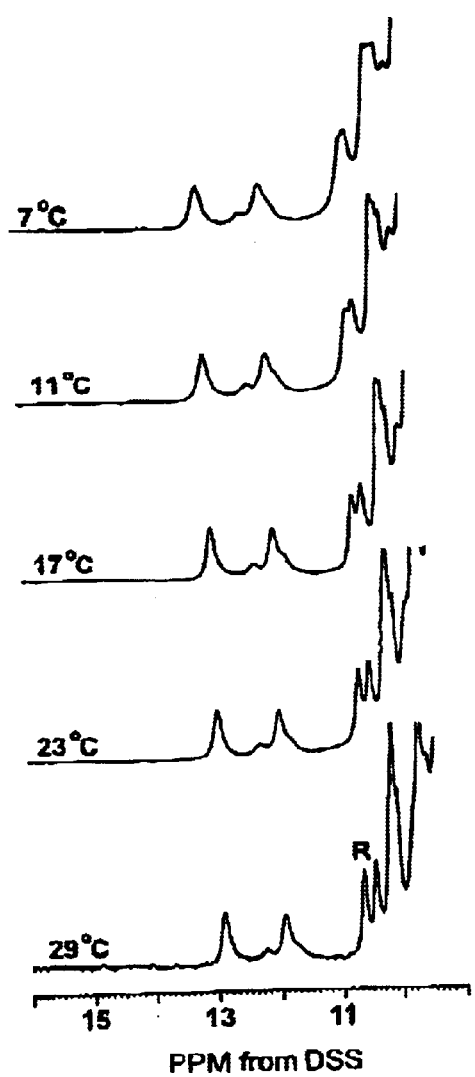
FIGS. 9A and 9B are 500-MHz spectra showing the exchangeable proton resonances of rHb (αL29F, βN108Q) in the CO form in 0.1 M sodium phosphate buffer at pH 7.0 at various temperatures (7° C., 11° C., 17° C., 23° C., 29° C.), without (FIG. 9A) and with (FIG. 9B) 4 mM IHP.
Figure 9B:
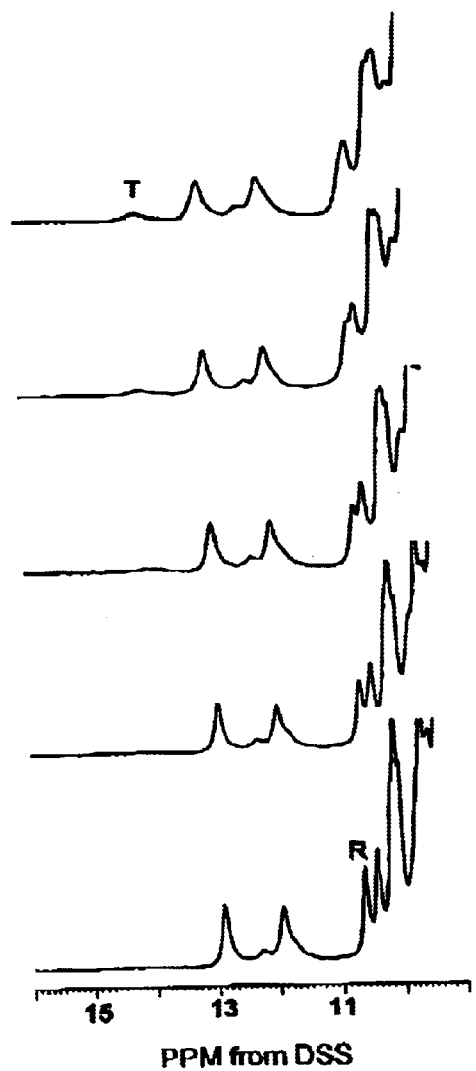

A unique feature of the rHbs of the present invention with low oxygen affinity and high cooperativity is the appearance of the T-marker at 14.2 ppm on lowering the temperature and/or adding IHP to these rHbs in the CO form (see Kim, et al. (1995); Ho, et al. (1998); Tsai, et al. (1999)). Studies on the temperature dependence of exchangeable proton resonances of rHbs in the CO form can be used to assess the structural effect on oxygen affinity. FIGS. 8A and 8B and FIGS. 9A and 9B show the exchangeable proton resonances of rHb ($\beta$N108Q) and rHb ($\alpha$L29F, $\beta$N08Q) in the CO form in the absence (FIGS. 8A, 9A) and presence (FIGS. 8B, 9B) of 4 mM IHP in 0.1 M sodium phosphate buffer as a function of temperature. The resonance at 14.2 ppm of rHb ($\beta$N108Q) is observable starting at 23° C. in 0.1 M phosphate at pH 7.0 in the presence of 4 mM IHP (FIG. 8B). The appearance of the T-marker in the presence of 4 mM IHP and at low temperature in the spectra of CO-ligated rHb ($\beta$N108Q) and rHb ($\alpha$L29F, $\beta$N108Q) indicates that the T-states of rHb ($\beta$N108Q) and rHb ($\alpha$L29F, $\beta$N108Q) are more stable than that of Hb A. However, this resonance in the spectra of Hb ($\alpha$L29F, $\beta$N108Q) has a much smaller intensity than that in the spectra of rHb ($\beta$N108Q) at low temperature, i.e., 11° C. and in the presence of 4 mM IHP.

Structural Studies of rHb ($\beta$L105W)

rHb ($\beta$L105W) was designed to form a new hydrogen bond with $\alpha$94Asp in the $\alpha_1\beta_2$ subunit interface in order to lower the oxygen binding affinity by stabilizing its deoxy quaternary structure. rHb ($\alpha$D94A, $\beta$L105W) and rHb ($\alpha$D94A) were constructed to provide evidence that $\beta$105Trp of rHb ($\beta$L105W) does form a new hydrogen bond with $\alpha$94Asp in the $\alpha_1\beta_2$ subunit interface of the deoxy quaternary structure. Multinuclear, multidimensional nuclear magnetic resonance (NMR) steadies on $^{15}$N-labeled rHb ($\beta$L105W) have identified the indole nitrogen-attached proton resonance of $\beta$105Trp for rHb ($\beta$L105W). $^1$H-NMR studies were used to investigate the structural basis for the low oxygen affinity of rHb ($\beta$L105W).

$^1$H-NMR Studies of the Structures of rHbs in the CO Form.

Figures 10A, 10B:
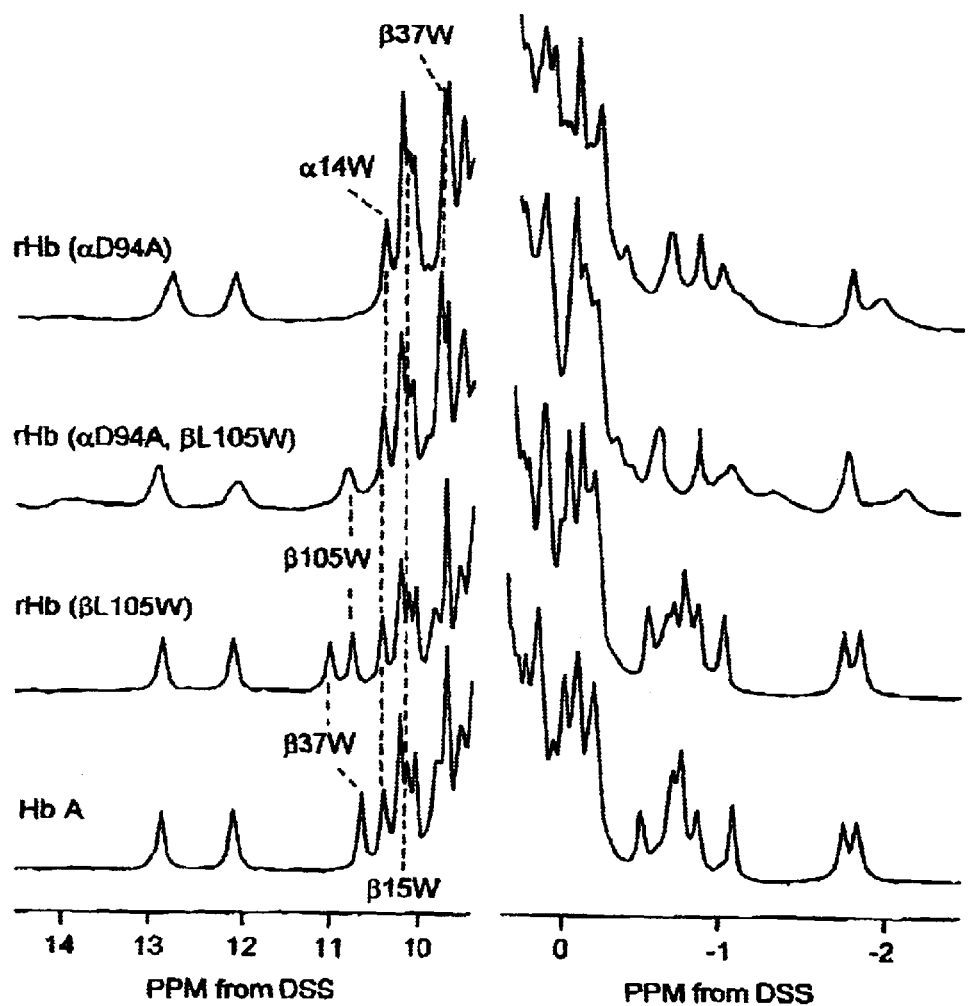
FIGS. 10A and 10B are 600-MHz $^1$H-NMR spectra showing exchangeable proton resonances (FIG. 10A) and ring-current shifted proton resonances (FIG. 10B) of 3–6% solutions of Hb A; rHb (βL05W); rHb (αD94A, βL105W); and rHb (αD94A) in the CO form in 0.1 M sodium phosphate at pH 7.0 and 29° C.

FIG. 10A shows the exchangeable proton resonances of Hb A, rHb ($\beta$L105W), rHb ($\alpha$D94A, $\beta$L105W), and rHb ($\alpha$D94A) in the CO form. The exchangeable proton resonances arise from the exchangeable protons in the subunit interfaces. Recent multinuclear, multidimensional NMR studies on the $^{15}$N-labeled rHb A have assigned the resonances at 10.6, 10.4 and 10.1 ppm to $\beta$37Trp, $\alpha$14TIP and $\beta$15Trp, respectively (Simplaceanu, et al. (2000)). The crystal structure of Hb A in the oxy form (Shaanan, (1983)) suggested the likely candidate to form an H-bond with $\beta$37Trp in the $\alpha_1\beta_2$ subunit interface is $\alpha$94Asp. The spectrum of rHb ($\beta$L105W) in the CO form shows an additional proton resonance in the region of exchangeable proton resonances (FIG. 10A). Since residues $\beta$37 and $\beta$105 are both located in the $\alpha_1\beta_2$ interface and are close in the R-quaternary structure (Shaanan, (1983)), the replacement of Leu by Trp at $\beta$105 position may cause the proton resonance of $\beta$37Trp to shift away from its original chemical shift. It is suspected that the extra resonance (at either 11.0 ppm or 10.8 ppm) originates from $\beta$105Trp. Heteronuclear, two-dimensional ("2D") NMR studies on the $^{15}$N-labeled rHb ($\beta$L105W) were, therefore, carried out to assign these resonances in the spectrum of rHb ($\beta$L105W). The spectrum of rHb ($\alpha$D94A) in the CO form shows that the resonance at 10.6 ppm (assigned to $\beta$37Trp in Hb A) is missing and a new resonance shows up at 9.7 ppm compared to the spectrum of Hb A (FIG. 10A). This result suggests that the shift of the resonance of $\beta$37Trp at 10.6 ppm to 9.7 ppm (closer to the water resonance) is due to the lack of an H-bond between $\alpha$94 and $\beta$37 in rHb ($\alpha$D94A) in the CO form. This result also confirms the assignment of the resonance at 10.6 ppm to the inter-subunit H-bond between $\alpha$94Asp and 37Trp. The spectrum of rHb ($\alpha$D94A, $\beta$L105W) in the CO form shows that one extra proton resonance appeared at 10.8 ppm compared to the spectrum of rHb ($\alpha$D94A). The resonance at 10.8 ppm was assigned to the indole NH of $\beta$105Trp of rHb ($\alpha$D94A, $\beta$L105W) and rHb ($\beta$L105W).

FIG. 10B shows the ring-current-shifted proton resonances of Hb A, rHb (βL105W), rHb (αD94A, βL105W), and rHb (αD94A) in the CO form. The ring-current-shifted resonances are very sensitive to the heme conformation and the tertiary structure of the heme pockets (Ho, (1992)). The spectrum for the ring-current-shifted proton resonances of rHb (βL105W) in the CO form differs only slightly from that of Hb A, while the spectra of rHb (αD94A, βL105W) and rHb (αD94A) are very different from that of Hb A. These differences imply that some adjustments of the heme conformation and/or the amino acid residues in the heme pockets occurred due to the mutation αD94A. Previous studies have shown that minor differences in the ring-current-shifted resonances are common features in many mutant rHbs. (Kim, et al. (1994); Kim, et al. (1995); Kim, et al. (1996); Sun, et al. (1997)).

Heteronuclear 2D NMR Studies on $^{15}$N-labeled rHb (βL105W) in the CO Form.

In older to assign the proton resonances at 11.0 ppm and 10.8 ppm in the $^1$H-NMR spectrum of rHb (βL105W), heteronuclear 2D NMR studies on $^{15}$N-labeled rHb (βL105W) in the CO form were performed. The results are shown in FIGS. 11A and 11B and FIGS. 12A–12D. FIGS. 11A and 11B show the 600-MHz HMQC spectra of $^{15}$N-labeled rHb (βL105W) and rHb A in the CO form. A doublet is observed at the ($^1$H$_{\epsilon1}$, $^{15}$N$_{\epsilon1}$) chemical shift coordinates for Trp residues because this spectrum was acquired without $^{15}$N decoupling. In general, the $^1$H$_{\epsilon1}$ resonances of Trp residues usually appear at ~9 to ~12 ppm (Cavanagh, et al. (1996); BioMagResBank (1999) (www.bmrb.wisc.edu/ref_info/statsel.htm) in the proton dimension, and their $^{15}$N$_{\epsilon1}$ resonances usually appear at ~121 to ~133 ppm (BioMagResBank) in the $^{15}$N dimension. The $^{15}$N chemical shifts for the proton resonances at 11.0 ppm and 10.8 ppm in the $^1$H-NMR spectrum of rHb (βL105W) are at 134 ppm and 129 ppm, respectively, suggesting that these resonances originate from a Trp residue. Since the chemical shift of a proton is much easier to be affected than that of nitrogen by its environment, the assignment of (11.0, 134) ppm to β37Trp and (10.8, 129) ppm to β105Trp was made (FIGS. 11A and 11B). This also agrees with what is shown in FIG. 10A. The HMQC spectrum also correlates the Trp $^{15}$N$_{\epsilon1}$ chemical shifts with the carbon-bound proton $^1$H$_{\epsilon1}$. As shown in FIGS. 11A and 11B, the $^1$H$_{\epsilon1}$ cross-peaks at (7.3, 129) and (7.1, 127) ppm are observed for α14Trp and β15Trp, respectively, in the spectra of both $^{15}$N-labeled rHb (βL105W) and rHb A in the CO form. Also observed are $^1$H$_{\epsilon1}$ cross-peaks (through two-bond coupling) at (7.4, 134) ppm with much weaker intensity for β37Trp in the spectrum of $^{15}$N-labeled rHb A in the CO form (results not shown in FIG. 11B). Since the $^1$H$_{\epsilon1}$ cross-peaks for β37Trp and β105Trp cannot be seen in the spectrum of $^{15}$N-labeled r Hb (βL105W) in the CO form (FIG. 11A), NOESY-HMQC experiments have been performed at different mixing times to provide more evidence for the present Trp assignments. As shown in FIGS. 12A–12D, the $^1$H$_{\epsilon1}$ and $^1$H$_{\zeta2}$ cross-peaks of all four Trp residues can be seen even at short mixing times. The intensities of these cross-peaks become weaker when the mixing time was 60 or 100 ms (FIGS. 12C, 12D). FIGS. 12A–12D also show that the chemical shifts of $^1$H$_{\epsilon1}$ and $^1$H$_{\zeta1}$ cross-peaks are very close to each other for β37Trp and β105Trp. All these results confirm the assignments for the Trp residues.

$^1$H-NMR Studies of the Structures of rHbs in the Deoxy Form.

FIG. 13A shows the hyperfine-shifted N$_\delta$H resonances of proximal histidines in the 300-MHz $^1$H-NMR spectra of Hb A, rHb (βL105W), rHb (αD94A, βL105W), and rHb (αD94A) in the deoxy form. The spectrum for the hyperfine-shifted N$_\delta$H resonances of proximal histidines of mutant rHbs in the deoxy form is very similar to that of Hb A. FIG. 13B shows the hyperfine-shifted and exchangeable proton resonances in the 300-MHz $^1$H-NMR spectra of Hb A, rHb (βL105W), rHb (αD94A, βL105W), and rHb (αD94A) in the deoxy form. The hyperfine-shifted proton resonances arise from the protons on the heme groups and their nearby amino acid residues due to the hyperfine, interactions between these protons and unpaired electrons of Fe(II) in the heme pocket (Ho (1992). The hyperfine-shifted proton resonances of rHb (βL105W) in the region +24 to +16 ppm are very similar to those of Hb A, but those for rHb (αD94A, βL105W) and rHb (αD94A) are somewhat different from these for Hb A. FIG. 13C shows the exchangeable proton resonances in the 300-MHz $^1$H-NMR spectra of Hb A, rHb (βL105W), rHb (αD94A, βL105W), and rHb (αD94A) in the deoxy form. The $^1$H resonance at ~14 ppm has been identified as the intersubunit H-bond between α42Tyr and β99Asp in the α$_1$β$_2$ interface in deoxy-Hb A, a characteristic feature of the deoxy (T)-quaternary structure of Hb A (Fung, et al. (1975)). The resonance at ~12.2 ppm has been assigned to the H-bond between α103His and β131Asp at the α$_1$β$_2$ interface (unpublished results). The resonance at ~11.1 ppm has been tentatively assigned to the H-bond between α94Asp and β37Trp at the (α$_1$β$_2$ interface (Fung, et al. (1975); Ishimori, et al. (1992)). Recent heteronuclear, multidimensional NMR studies on the $^{15}$N-labeled rHb A have assigned the resonance at ~13.0 ppm to α122His, and confirmed the assignment of the resonance at ~11.1 ppm to β37Trp (unpublished results). The spectrum of rHb (βL105W) in the deoxy form shows an additional proton resonance appearing in the region of the exchangeable proton resonances (FIG. 13C). This suggests that the extra resonance at 12.7 ppm originates from β105Trp. Due to the lack of an H-bond between residues α94 and β37 in rHb (αD94A) in the deoxy form, the resonance for β37Trp should shift away from its original chemical shift and closer to the water resonance (similar to what was observed in its CO form). The spectrum of rHb (αD94A) in the deoxy form shows that the resonance at ~11.1 ppm (assigned to β37Trp in Hb A) is missing (FIG. 13C). However, it is not clear what is the new chemical shift for β37Trp in rHb (αD94A) in the deoxy form. The spectrum of rHb (αD94A, βL105W) in the deoxy form shows an extra proton resonance appearing at 11.1 ppm compared to that of rHb (αD94A). It appears that this resonance originates from β105Trp of rHb (αD94A, βL105W). The chemical shift for the NH resonance of β105Trp in rHb (βL105W) shifts upfield 1.7 ppm and closer to the water resonance when α94Asp is replaced by Ala in rHb (αD94A, βL105W) (FIG. 13C). These results indicate that a new H-bond forms between β105Trp and α94Asp in rHb (βL105W) in the deoxy form.

Heteronuclear 2D NMR Studies on $^{15}$N-labeled rHb (βL105W) in the Deoxy Form.

Figure 14:
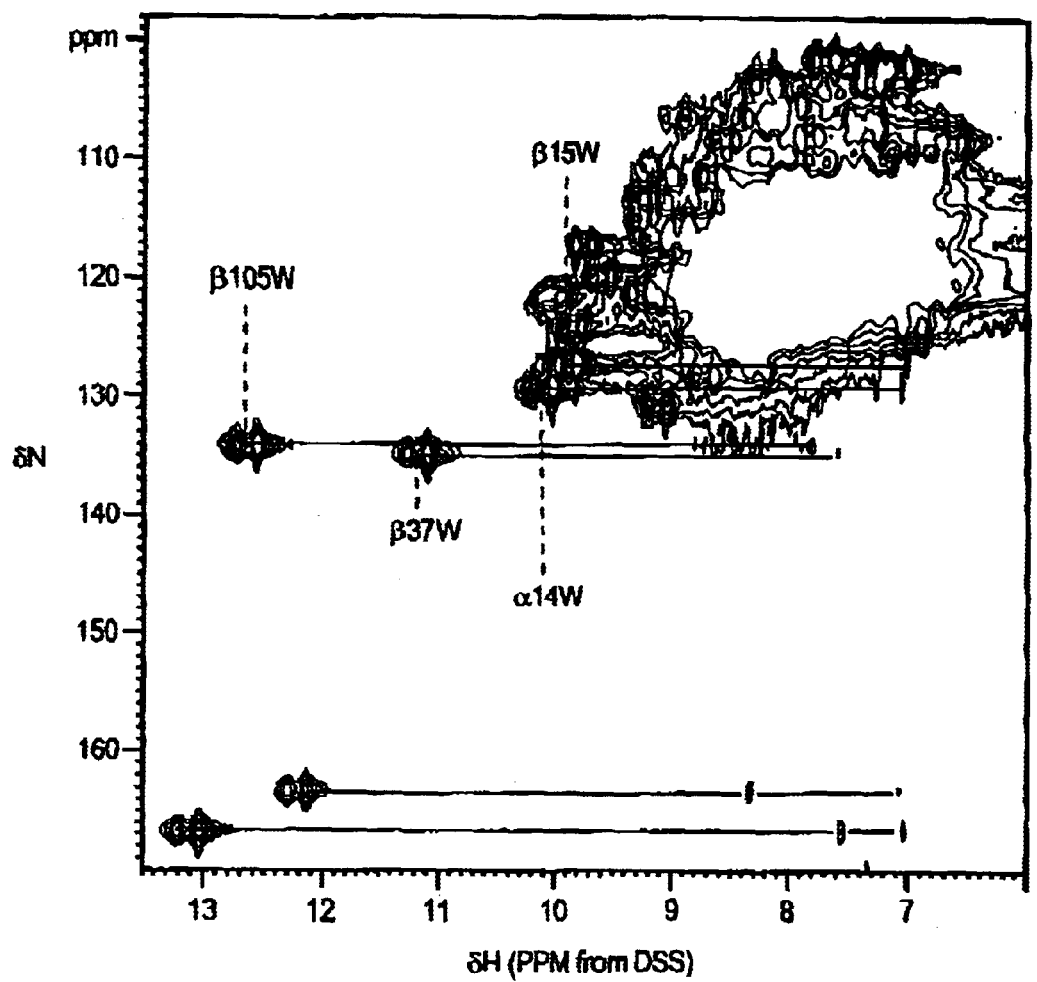
FIG. 14 is a 600-MHz 2D HMQC spectrum of 5–8% solutions of $^{15}$N-labeled rHb (βL105W) in the deoxy form in 90% $H_2O$/10% $D_2O$ in 0.1 M sodium phosphate at pH 7.0 and 29° C.
Figure 15A:
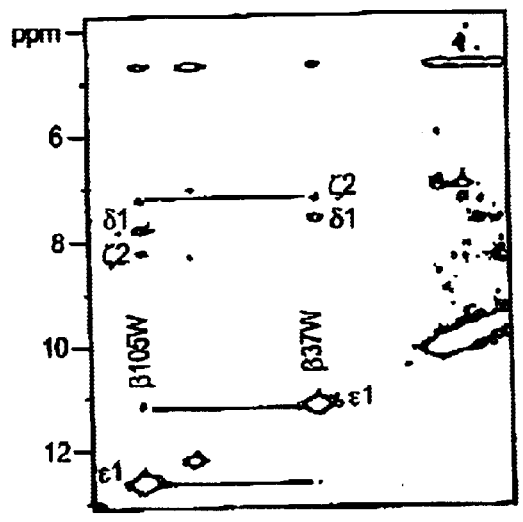
FIGS. 15A–15D are 600-MHz 2D NOESY-HMQC spectra of 5% solution of $^{15}$N-labeled rHb (βL105W) in the deoxy form in 90% $H_2O$/10% $D_2O$ in 0.1 M sodium phosphate at pH 7.0 and 29° C. recorded at various mixing times: 15 ms (FIG. 15A); 30 ms (FIG. 15B); 60 ms (FIG. 15C); and 100 ms (FIG. 15D). The solid line between two cross peaks indicates the inter-residue NOE effect between the $^1H_{\epsilon 1}$ of one residue and the $^1H_{\epsilon 1}$ and $^1H_{\zeta 2}$ of the other residue for β37Trp and β105Trp.
Figure 15B:
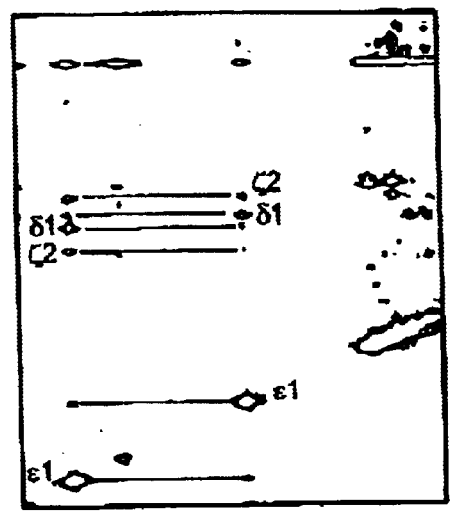
Figure 15C:
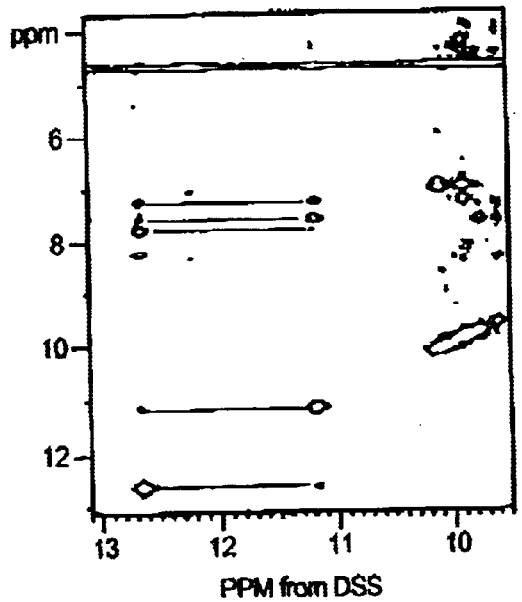
Figure 15D:
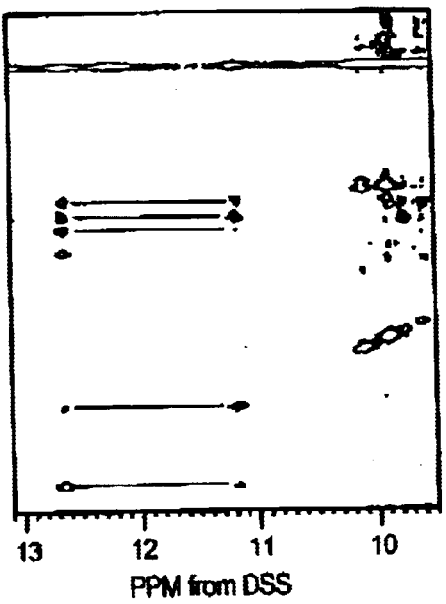

In order to confirm the assignment of resonance at 12.7 ppm to β105Trp in the $^1$H-NMR spectrum of rHb (βL105W) in the deoxy form, heteronuclear 2D NMR experiments on $^{15}$N-labeled rHb (βL105W) in the deoxy form were performed (FIGS. 14 and 15A–15D). FIG. 14 shows the 600-MHz HMQC spectrum of $^{15}$N-labeled rHb (βL105W) in the deoxy form. The $^{15}$N chemical shift for the proton resonance at 12.7 ppm in the $^1$H-NMR spectrum of rHb (βL105W) is at 134 ppm, suggesting that this resonance originates from a tryptophan residue. Also observed are the $^1$Hδ$_1$ cross-peaks of Trp $^{15}$N$_{\epsilon1}$ at (7.8, 134), (7.6, 135), (7.1, 129), and (7.0, 127) ppm for β105Trp, β37Trp, α14Trp and β15Trp, respectively, in the HMQC spectrum of $^{15}$N-labeled r Hb (βL105W) in the deoxy form. Also observed are the $^1H_{\epsilon 1}$ and $^1H_{\zeta 2}$ cross-peaks of His $^{15}N_{\epsilon 2}$ for α103His at (8.3, 163) and (7.1, 163) ppm, respectively, and for α122His at (7.6, 167) and (7.0, 167) ppm, respectively. The NOESY-HMQC experiments were also performed at different mixing times to provide more evidence for the present assignments and to investigate the micro-environment for β105Trp in rHb (βL105W) in the deoxy form. For β105Trp (at 12.7 ppm), its $^1H\delta_1$ and $1H\zeta_2$ cross-peaks at 7.8 and 8.2 ppm, respectively, can be observed at all four mixing times (FIGS. 15A–15D). For β37Trp (at 11.2 ppm), its $^1H\delta_1$ and $^1H\zeta_2$ cross-peaks at 7.6 and 7.3 ppm, respectively, also can be observed at all four mixing times (FIGS. 15A–15D). In addition, also observed is the NOE effect between residues of β105Trp and β37Trp in the NOESY-HMQC spectra of $^{15}$N-labeled rHb (βL105 W) in the deoxy form as shown in FIGS. 15A–15D.

The Effects of IHP and Temperature on the Spectra of Hbs in the CO Form

Figure 16A:
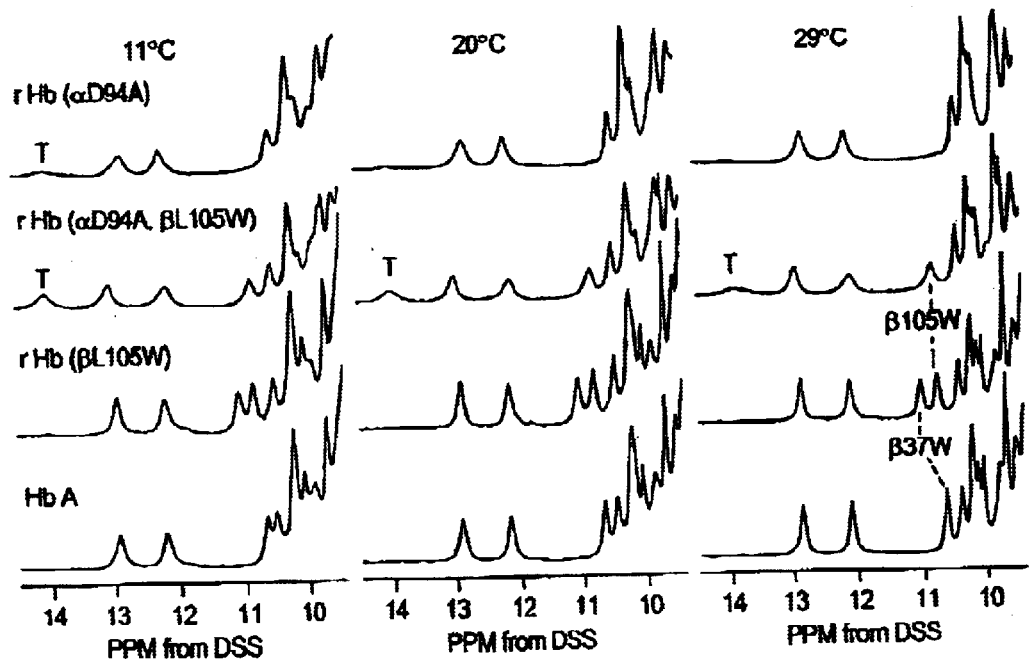
FIGS. 16A–16B show exchangeable proton resonances in 600-MHz $^1$H-NMR spectra of 3–6% solutions of Hb A; rHb (βL105W); rHb (αD94A, βL105W); and rHb (αD94A) in the CO form in 0.1 M sodium phosphate at pH 7.0 and at 11°, 20°, and 29° C. in the absence (FIG. 16A) and presence (FIG. 16B) of 2 mM IHP.
Figure 16B:
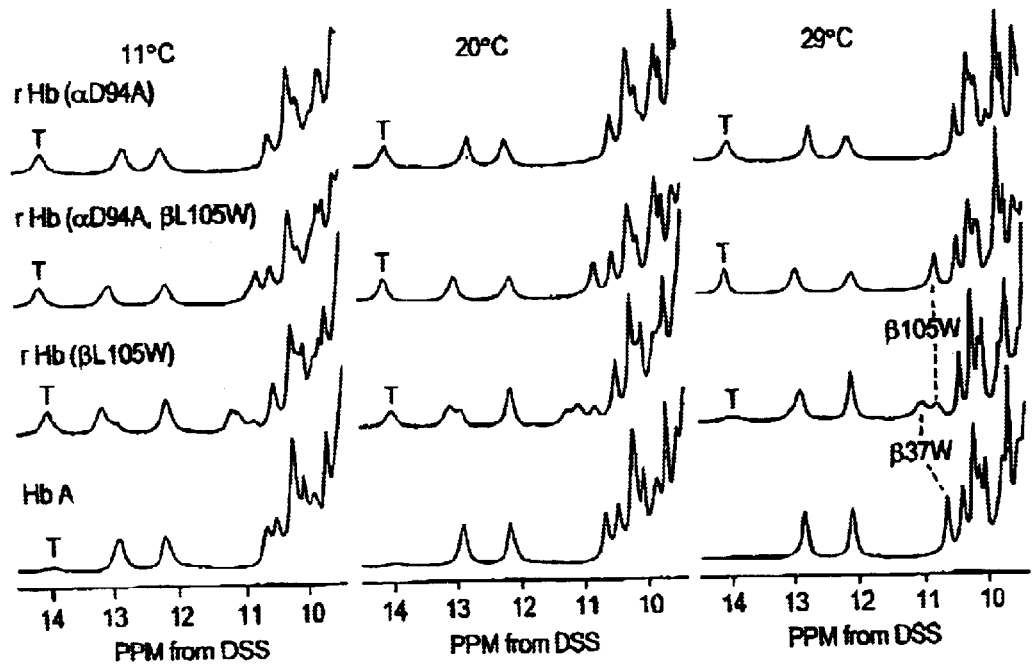

FIGS. 16A and 16B show the exchangeable protons resonances of Hb A, rHb (βL105W), rHb (αD94A, βL105W), and rHb (αD94A) in the CO form in the absence (FIG. 16A) and presence (FIG. 16B) of IHP at 11, 20, and 29° C. In the absence of IHP, the T marker can be observed only in the spectra of rHb (αD94A, βL105 W) at the lower temperature. In the presence of IHP, the T marker can be observed in the spectra of all three mutant rHbs. These results have shown that these mutant rHbs can switch from the R-structure to the T-structure without changing their ligation state when the temperature is lowered and/or when IHP is is added. Besides the appearance of the T marker, the spectra of rHb (βL105W) in the CO form in the presence of IHP also show several differences compared to those in the absence of IHP. In the presence of IHP, new peaks at 13.1 and 11.2 ppm appear to gradually grow from the nearby resonances at 12.9 and 11.0 (or 10.8) ppm, respectively, when the temperature is lowered (FIG. 16B).

In order to monitor these changes, more detailed HSQC experiments have been performed for $^{15}$N-labeled rHb (βL105W) in the absence and the presence of IHP. In the presence of IHP, the HSQC experiments have also been performed at lower temperatures (FIGS. 17A–17D). In the presence of IHP at 29° C., the ($^1H_{\epsilon 1}$, $^{15}N_{\epsilon 1}$) cross-peak at (11.0, 134) ppm for β37Trp disappears. The ($^1H_{\epsilon 1}$, $^{15}N_{\epsilon 1}$) cross-peak at (10.8, 129) ppm for β105Trp is much weaker in the presence of IHP at 29° C. compared to that in the absence of IHP (FIGS. 17A and 17B). When the temperature is lowered in the presence of IHP, the cross-peak at (11.0, 134) ppm reappears and two new cross-peaks appear at (11.0, 131) and (10.9, 130) ppm (FIGS. 17C and 17D). It appears that these two new cross peaks originate from β37Trp and β105Trp.

Figure 18A:
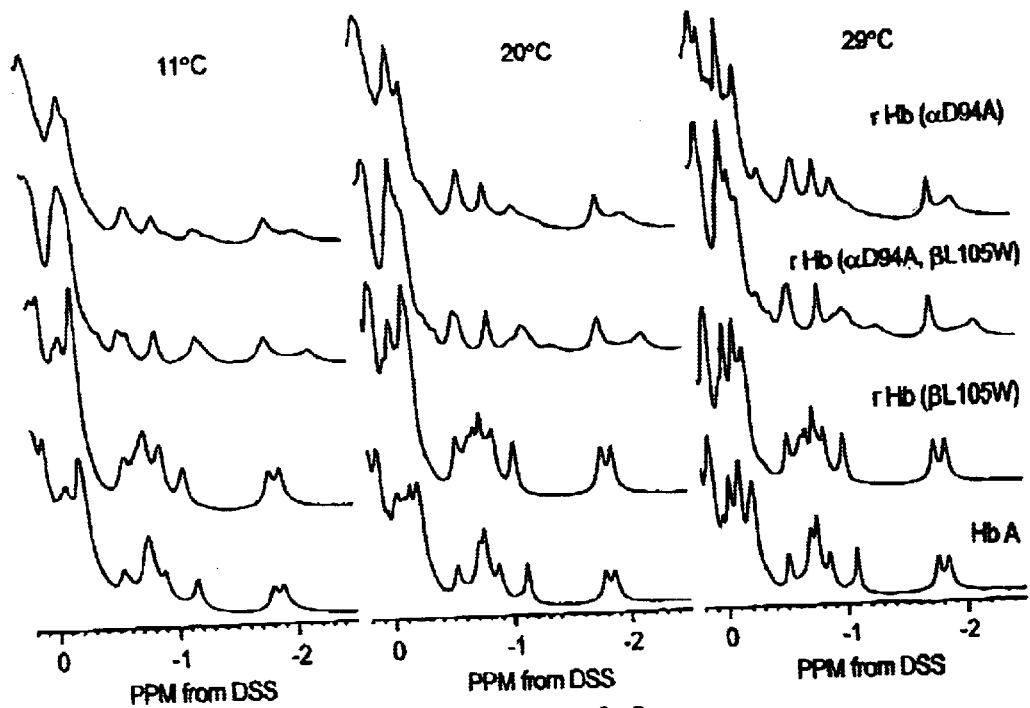
FIGS. 18A–18B show ring-current shifted proton resonances in 600-MHz $^1$H-NMR spectra of 3–6% solutions of Hb A; rHb (βL105W); rHb (αD94A, , βL105W); and rHb (αD94A) in the CO form in 0.1 M sodium phosphate at pH 7.0 and various temperatures in the absence (FIG. 18A) and presence (FIG. 18B) of 2 mM IHP.
Figure 18B:
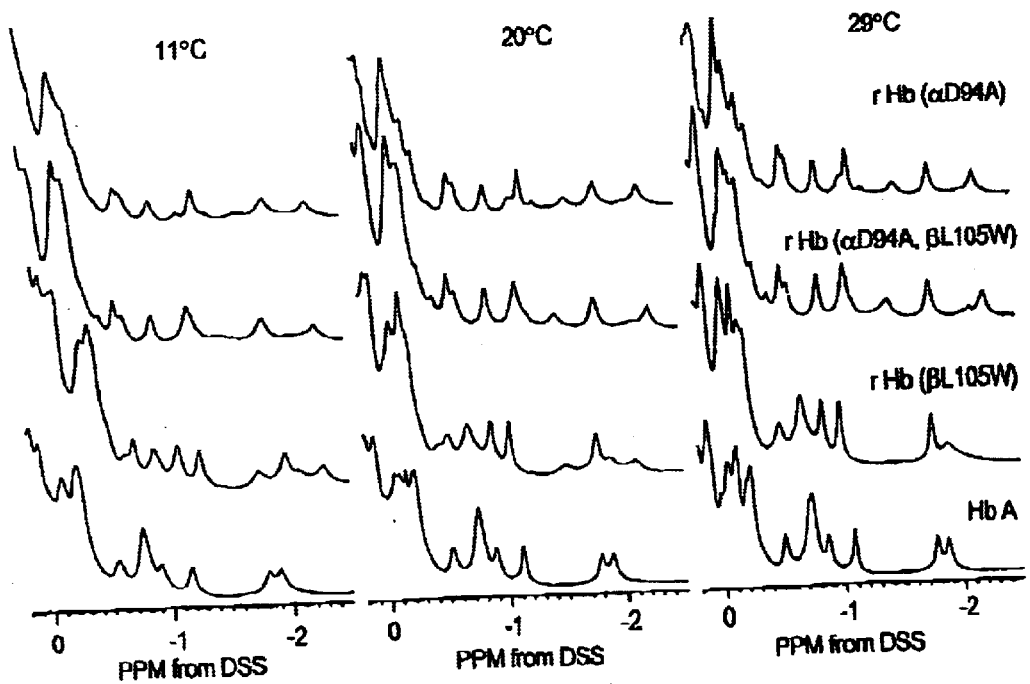

FIGS. 18A and 18B show the ring-current-shifted proton resonances of Hb A, rHb (βL105w), rHb (αD94A, βL105W), and rHb (αD94A) in the CO form in the absence and presence of IHP at 11, 20, and 29° C. The ring-current-shifted proton resonances of rHb (βL105W) in the CO form differ only slightly from those of Hb A in the absence of IHP, while they are very different from those of Hb A in the presence of IHP. The ring-current-shifted proton resonances of rHb (αD94A, βL105W) and rHb (αD94A) in the CO form are very different from those of Hb A in both the absence and presence of IHP, but they are very similar to each other in the presence of IHP. In addition, the ring-current-shifted proton resonances of rHb (βL105W) in the CO form in the presence of IHP turn out to be very similar to those of rHb (αD94A/βL105W) and rHb (αD94A) when the temperature is lowered (FIG. 18B). It is believed that the spectra for the ring-current-shifted proton resonances of rHb (αD94A, βL105W) and rHb (αD94A) in the CO form in the presence IHP represent one type of spectrum for rHbs in the CO form with a stable T-structure. Therefore, the differences in heme pocket conformations between mutant rHbs and Hb A also suggest that these mutant rHbs are much easier to switch from the R-structure to T-structure in light of the T-marker from the exchangeable proton resonances. The resonances at −1.8 and −1.9 ppm have been assigned to the heme pocket distal valine (E11) of α- and β-chains of Hb A, respectively (Dalvit, C., et al., *Biochemistry* 24: 3398 (1985) and Craescu, C. T., et al., *Eur. J. Biochem* 181: 87 (1989), the disclosures of which are incorporated herein by reference). Compared to the spectra of Hb A, the resonance of distal valine (E11) of β-chain seems to be affected more in the spectra of mutant rHbs, especially in the presence of IHP, than that of α-chain (FIGS. 18A and 18B). These results imply that the structural switching from the R- to the T-structure induced by IHP, temperature, or the mutations described herein might occur mainly in the β-chain.

Appropriately cross-linked rHb (βN108Q) and/or rHb (βL105W) can be incorporated into a hemoglobin-based blood substitute or therapeutic hemoglobin that is physiologically acceptable for use in clinical or veterinary medicine according to methods know in the art. See, for exemple, R. M. Winslow, et al. Eds. *Blood Substitutes Physiological Basis Of Efficacy*, pp. 82–84 (Birkhauser, Boston, Mass.) (1995), the disclosure of which is incorporated herein by reference. The hemoglobin of the present invention may also be advantageously used as a treatment for conditions such as septic shock, prevention of anaphylactic shock during dialysis.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A non-naturally occurring mutant human hemoglobin wherein the leucine residue at position 105 of the β-chains (SEQ ID NO:8) is replaced by a tryptophan residue.

2. The hemoglobin of claim 1 possessing low oxygen affinity as compared to normal human adult hemoglobin.

3. The hemoglobin of claim 2 further possessing high cooperativity in oxygen binding comparable to normal human adult hemoglobin.

4. The hemoglobin of claim 3 further possessing increased stability against autooxidation.

5. The hemoglobin of claim 1 which is produced recombinantly.

6. rHb (βL105W) (SEQ ID NO:8).

7. rHb (βL105W) (SEQ ID NO:8), derived from cells transformed with pHE7004.

8. An artificial mutant hemoglobin which in a cell-free enviornment has oxygen binding properties comparable to those of human normal adult hemoglobin in red blood cells wherein said hemoglobin contains a mutation such that the leucine residue at position 105 of the β-chains is tryptophan (SEQ ID NO: 8).

9. The hemoglobin of claim 8 which is produced recombinantly.

10. A non-toxic pharmaceutical composition comprising a non-naturally occurring mutant hemoglobin wherein the leucine residue at position 105 of the β-chains is replaced by a tryptophan residue (SEQ ID NO:8) in a pharmaceutically acceptable carrier.

11. The composition of claim 10 wherein said hemoglobin in a cell-free environment has oxygen binding properties lower than that of human normal adult hemoglobin.

12. The composition of claim 11 wherein said hemoglobin is rHb (β105W) (SEQ ID NO: 8).

13. A non-naturally occurring low oxygen affinity mutant hemoglobin that has oxygen binding properties comparable to those of human normal adult hemoglobin in the presence of the allosteric effector 2,3-bisphoshoglycerate, wherein the leucine residue at position 105 of each of the β-chains is replaced by a tryptophan residue (SEQ ID NO:8).

14. A non-naturally occurring mutant human hemoglobin wherein the leucine residue at position 105 of the β-chains is replaced by a tryptophan residue (SEQ ID NO:8), wherein said hemoglobin possesses oxygen-binding properties of oxygen affinity as measured by $P_{50}$ and cooperativity as measured by the Hill coefficient ($n_{max}$) and similar to those of Hb A in the presence of the allosteric effector 2,3-bisphosphoglycerate as follows: $P_{50}$ about 28.2 mm Hg, $n_{max}$ about 2.50 in 0.1 M sodium phosphate at pH 7.4 and 29° C.

15. A method of treating a human subject comprising administering to said subject a nontoxic composition comprising an artificial mutant hemoglobin, wherein said artificial mutant hemoglobin is rHb (βL105W) (SEQ ID NO: 8).

* * * * *

UNITED STATES PATENT AND TRADEMARK OFFICE
CERTIFICATE OF CORRECTION

PATENT NO. : 6,812,328 B2
DATED : November 2, 2004
INVENTOR(S) : Ho et al.

It is certified that error appears in the above-identified patent and that said Letters Patent is hereby corrected as shown below:

Column 28,
Line 49, delete "2.50" and substitute -- 2.60 -- therefor.

Signed and Sealed this

First Day of February, 2005

JON W. DUDAS
*Director of the United States Patent and Trademark Office*